(12) United States Patent
Liu

(10) Patent No.: US 11,807,685 B2
(45) Date of Patent: Nov. 7, 2023

(54) ANTI-CD47 ANTIBODY AND USES THEREOF

(71) Applicant: THE UAB RESEARCH FOUNDATION, Birmingham, AL (US)

(72) Inventor: Xiaoguang Margaret Liu, Vestavia Hills, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 17/817,448

(22) Filed: Aug. 4, 2022

(65) Prior Publication Data

US 2023/0054375 A1 Feb. 23, 2023

Related U.S. Application Data

(60) Provisional application No. 63/229,807, filed on Aug. 5, 2021.

(51) Int. Cl.
| | |
|---|---|
| *C12P 21/08* | (2006.01) |
| *A61K 39/395* | (2006.01) |
| *A61K 47/68* | (2017.01) |
| *C07K 16/28* | (2006.01) |
| *C07K 16/30* | (2006.01) |
| *A61P 35/00* | (2006.01) |
| *A61K 39/00* | (2006.01) |

(52) U.S. Cl.
CPC ...... *C07K 16/2803* (2013.01); *A61K 47/6803* (2017.08); *A61K 47/6849* (2017.08); *A61P 35/00* (2018.01); *A61K 47/6809* (2017.08); *A61K 47/68031* (2023.08); *A61K 47/68033* (2023.08); *A61K 47/6851* (2017.08); *A61K 47/6877* (2017.08); *A61K 2039/505* (2013.01); *C07K 16/30* (2013.01); *C07K 2317/24* (2013.01); *C07K 2317/56* (2013.01); *C07K 2317/565* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 4,137,230 A | 1/1979 | Hashimoto et al. |
| 4,151,042 A | 4/1979 | Higashide et al. |
| 4,248,870 A | 2/1981 | Miyashita et al. |
| 4,256,746 A | 3/1981 | Miyashita et al. |
| 4,260,608 A | 4/1981 | Miyashita et al. |
| 4,265,814 A | 5/1981 | Hashimoto et al. |
| 4,294,757 A | 10/1981 | Asai |
| 4,307,016 A | 12/1981 | Asai et al. |
| 4,308,268 A | 12/1981 | Miyashita et al. |
| 4,308,269 A | 12/1981 | Miyashita et al. |
| 4,309,428 A | 1/1982 | Miyashita et al. |
| 4,313,946 A | 2/1982 | Powell et al. |
| 4,317,821 A | 3/1982 | Miyashita et al. |
| 4,322,348 A | 3/1982 | Lamparsky |
| 4,331,598 A | 5/1982 | Hasegawa et al. |
| 4,361,650 A | 11/1982 | Asai et al. |
| 4,362,663 A | 12/1982 | Kida et al. |
| 4,364,866 A | 12/1982 | Asai et al. |
| 4,371,533 A | 2/1983 | Akimoto et al. |
| 4,424,219 A | 1/1984 | Hashimoto et al. |
| 4,450,254 A | 5/1984 | Isley et al. |
| 4,663,149 A | 5/1987 | Eckenhof et al. |
| 4,816,567 A | 3/1989 | Cabilly et al. |
| 5,053,394 A | 10/1991 | Ellestad et al. |
| 5,208,020 A | 5/1993 | Chari et al. |
| 5,225,539 A | 7/1993 | Winter |
| 5,416,064 A | 5/1995 | Chari et al. |
| 5,530,101 A | 6/1996 | Queen et al. |
| 5,585,089 A | 12/1996 | Queen et al. |
| 5,635,483 A | 6/1997 | Pettit et al. |
| 5,639,641 A | 6/1997 | Pedersen et al. |
| 5,693,762 A | 12/1997 | Queen et al. |
| 5,712,374 A | 1/1998 | Kuntsmann et al. |
| 5,714,352 A | 2/1998 | Jakobovits |
| 5,714,586 A | 2/1998 | Kuntsmann et al. |
| 5,723,323 A | 3/1998 | Kauffman et al. |
| 5,739,116 A | 4/1998 | Hamann et al. |
| 5,750,373 A | 5/1998 | Garrard et al. |
| 5,763,192 A | 6/1998 | Kauffman et al. |
| 5,766,886 A | 6/1998 | Studnicka et al. |
| 5,767,285 A | 6/1998 | Hamann et al. |
| 5,770,701 A | 6/1998 | McGahren et al. |

(Continued)

FOREIGN PATENT DOCUMENTS

| | | |
|---|---|---|
| EP | 229246 A2 | 7/1987 |
| EP | 425235 B1 | 2/1991 |

(Continued)

OTHER PUBLICATIONS

Al-Lazikani et al., "Standard Conformations for the Canonical Structures of Immunoglobulins," Journal of Molecular Biology, 1997, vol. 273, No. 4, pp. 927-948.

Al-Mahmood et al., "Metastatic and triple-negative breast cancer: challenges and treatment options," Drug Delivery and Translational Research, 2018, vol. 8, pp. 1483-1507.

Almåsbak et al., "CAR T Cell Therapy: A Game Changer in Cancer Treatment," Journal of Immunology Research, 2016, vol. 2016, Article 5474602, 10 pages.

Bardia et al., "Sacituzumab Govitecan in Metastatic Triple-Negative Breast Cancer," The New England Journal of Medicine, 2021, vol. 384, pp. 1529-1541.

(Continued)

*Primary Examiner* — Thea D' Ambrosio
*Assistant Examiner* — Brianna K Swartwout
(74) *Attorney, Agent, or Firm* — Thomas | Horstemeyer, LLP

(57) ABSTRACT

Disclosed is an antibody that selectively binds CD47 on tumor cells. Also disclosed is a method for treating cancer in a subject, comprising administering to the subject an effective amount of the antibody disclosed.

12 Claims, 10 Drawing Sheets

Specification includes a Sequence Listing.

(56) References Cited

U.S. PATENT DOCUMENTS

| | | | |
|---|---|---|---|
| 5,770,710 A | 6/1998 | McGahren et al. |
| 5,773,001 A | 6/1998 | Hamann et al. |
| 5,780,588 A | 7/1998 | Pettit et al. |
| 5,814,476 A | 9/1998 | Kauffman et al. |
| 5,817,483 A | 10/1998 | Kauffman et al. |
| 5,824,514 A | 10/1998 | Kauffman et al. |
| 5,877,296 A | 3/1999 | Hamann et al. |
| 5,885,793 A | 3/1999 | Griffiths et al. |
| 5,969,108 A | 10/1999 | McCafferty et al. |
| 5,976,862 A | 11/1999 | Kauffman et al. |
| 6,172,197 B1 | 1/2001 | McCafferty et al. |
| 6,180,370 B1 | 1/2001 | Queen et al. |
| 6,204,023 B1 | 3/2001 | Robinson et al. |
| 6,300,064 B1 | 10/2001 | Knappik et al. |
| 6,413,746 B1 | 7/2002 | Field |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,653,068 B2 | 11/2003 | Frisch et al. |
| 6,706,484 B1 | 3/2004 | Knappik et al. |
| 7,264,963 B1 | 9/2007 | Knappik et al. |
| 7,342,110 B2 | 3/2008 | Hoffee et al. |
| 7,538,195 B2 | 5/2009 | Singh et al. |
| 7,557,189 B2 | 7/2009 | Hoffee et al. |
| 7,612,062 B2 | 11/2009 | Gregson et al. |
| 7,776,814 B2 | 8/2010 | Dömling et al. |
| 2008/0185795 A1 | 8/2008 | Cheng et al. |
| 2008/0312425 A1 | 12/2008 | Bonnerjea et al. |
| 2008/1770748 | 12/2008 | Bonnerjea et al. |
| 2009/0187005 A1 | 7/2009 | Gagnon |
| 2011/0256144 A1* | 10/2011 | Okano ............... C07K 16/3053 424/139.1 |
| 2012/0164205 A1* | 6/2012 | Baum ................ C12N 15/8286 435/254.11 |
| 2013/0224228 A1* | 8/2013 | Jackson ................. A61P 35/00 530/331 |
| 2020/0255515 A1* | 8/2020 | Sung ...................... A61P 35/02 |

FOREIGN PATENT DOCUMENTS

| | | |
|---|---|---|
| WO | 90/14424 A1 | 11/1990 |
| WO | 90/14430 A1 | 11/1990 |
| WO | 90/14443 A1 | 11/1990 |
| WO | 1993/21232 A1 | 10/1993 |
| WO | 2000/012507 A2 | 3/2000 |
| WO | 2002/088172 A2 | 11/2002 |
| WO | 04/009823 A1 | 1/2004 |
| WO | 2005/040170 A2 | 5/2005 |
| WO | 2005/085251 A1 | 9/2005 |
| WO | 2005/110423 A2 | 11/2005 |
| WO | 2007/039752 A1 | 4/2007 |
| WO | 2012/019123 A1 | 2/2012 |

OTHER PUBLICATIONS

Bardia et al., "Sacituzumab Govitecan-hziy in Refractory Metastatic Triple-Negative Breast Cancer," The New England Journal of Medicine, 2019, vol. 380, pp. 741-751.

Boerner et al., "Production of Antigen-Specific Human Monoclonal Antibodies from in Vitro-Primed Human Splenocytes," The Journal of Immunology, Jul. 1, 1991, vol. 147, No. 1, pp. 86-95.

Boger et al., "CC-1065 and the duocarmycins: Unraveling the keys to a new class of naturally derived DNA alkylating agents," Proceedings of the National Academy of Sciences USA, Apr. 1995, vol. 92, pp. 3642-3649.

Campbell et al., "MCL-1 is a prognostic indicator and drug target in breast cancer," Cell Death & Disease, 2018, vol. 9, No. 19, 14 pages.

Carter et al., "Humanization of an anti-p185HER2 antibody for human cancer therapy," Proceedings of the National Academy of Sciences USA, May 1992, vol. 89, pp. 4285-4289.

Chao et al., "Anti-CD47 antibody synergizes with rituximab to promote phagocytosis and eradicate non-Hodgkin lymphoma," Author manuscript, Cell, Sep. 3, 2010, vol. 142, No. 5, pp. 699-713, 28 pages.

Chari et al., "Immunoconjugates Containing Novel Maytansinoids: Promising Anticancer Drugs," Cancer Research, Jan. 1, 1992, vol. 52, pp. 127-131.

Cheung et al., "Anti-Folate Receptor Alpha-Directed Antibody Therapies Restrict the Growth of Triple-negative Breast Cancer," Clinical Cancer Research, Oct. 15, 2018, vol. 24, No. 20, pp. 5098-5111.

Chothia et al., "Canonical Structures for the Hypervariable Regions of Immunoglobulins," Journal of Molecular Biology, 1987, vol. 196, pp. 901-917.

Dai et al., "Chimeri Antigen Receptors Modified T-Cells for Cancer Therapy," Journal of the National Cancer Institute, 2016, vol. 108, No. 7, 14 pages.

Flynn et al., "Anti-EGFR Therapy: Mechanism and Advances in Clinical Efficacy in Breast Cancer," Journal of Oncology, 2009, vol. 2009, Article 526963, 16 pages.

Frontera et al., "IgA Fc-folate conjugate activates and recruits neutrophils to directly target triple-negative breast cancer cells," Breast Cancer Research and Treatment, 2018, vol. 172, pp. 551-560.

Gardai et al., "Cell-Surface Calreticulin Initiates Clearance of Viable or Apoptotic Cells through trans-Activation of LRP on the Phagocyte," Cell, Oct. 21, 2005, vol. 123, pp. 321-334.

Gluzman, Yakov, "SV40-Transformed Simian Cells Support the Replication of Early SV40 Mutants," Cell, Jan. 1981, vol. 23, pp. 175-182.

Hinman et al., "Preparation and Characterization of Monoclonal Antibody Conjugates of the Calicheamicins: A Novel and Potent Family of Antitumor Antibiotics," Cancer Research, Jul. 15, 1993, vol. 53, pp. 3336-3342.

Hoogenboom et al., "By-passing Immunisation: Human Antibodies from Synthetic Repertoires of Germline VH Gene Segments Rearranged in Vitro," Journal of Molecular Biology, 1992, vol. 227, pp. 381-388.

Huang et al., "Targeting CD47: the achievements and concerns of current studies on cancer immunotherapy," Journal of Thoracic Disease, Feb. 2017, vol. 9, No. 2, pp. E168-E174.

Inao et al., "Bcl-2 inhibition sensitizes triple-negative human breast cancer cells to doxorubicin," Oncotarget, 2018, vol. 9, No. 39, pp. 25545-25556.

Innes et al., "Significance of the metastasis-inducing protein AGR2 for outcome in hormonally treated breast cancer patients," British Journal of Cancer, 2006, vol. 94, pp. 1057-1065.

Inouye et al., "Single-step purification of F(ab')2μ fragments of mouse monoclonal antibodies (immunoglobulins M) by hydrophobic interaction high-performance liquid chromatography using TSKgel Ether-5PW," Journal of Biochemical and Biophysical Methods, 1993, vol. 26, pp. 27-39.

Kaur et al., "Biological evaluation of tubulysin A: a potential anticancer and antiangiogenic natural product," Biochemistry Journal, 2006, vol. 396, No. 2, pp. 235-242.

Kershaw et al., "Making Macrophages Eat Cancer," Science, Jul. 5, 2013, vol. 341, pp. 41-43.

Khalil et al., "Mechanism of Action of Tubulysin, an Antimitotic Peptide from Myxobacteria," ChemBioChem, 2006, vol. 7, pp. 678-683.

Khan et al., "Role of miRNA-Regulated Cancer Stem Cells in the Pathogenesis of Human Malignancies," Cells, 2019, vol. 8, No. 840, 33 pages.

Kunert et al., "Advances in recombinant antibody manufacturing," Applied Microbiology and Biotechnology, 2016, vol. 100, No. 8, pp. 3451-3461.

Lebert et al., "Advances in the systemic treatment of triple-negative breast cancer," Current Oncology, Jun. 2018, vol. 25, Supp. 1, pp. S142-S150.

Lee et al., "Calicheamicins, A Novel Family of Antitumor," The Journal of Antibiotics, Jul. 1989, vol. 42, No. 7, pp. 1071-1087.

(56) References Cited

OTHER PUBLICATIONS

Lehmann et al., "Identification of human triple-negative breast cancer subtypes and preclinical models for selection of targeted therapies," The Journal of Clinical Investigation, 2011, vol. 121, No. 7, 18 pages.

Lehmann et al., "Refinement of Triple-Negative Breast Cancer Molecular Subtypes: Implications for Neoadjuvant Chemotherapy Selection," PLoS ONE, 2016, vol. 11, No. 6, 22 pages.

Liedtke et al., "Response in Neoadjuvant Therapy and Long-Term Survival in Patients With Triple-Negative Breast Cancer," Journal of Clinical Oncology, Mar. 10, 2008, vol. 26, No. 8, pp. 1276-1281.

Liu et al., "CD47 Blockage Triggers T cell-mediated Destruction of Immunogenic Tumors," Author manuscript, Nature Medicine, Oct. 2015, vol. 21, No. 10, pp. 1209-1215, 22 pages.

Liu et al., "Eradication of large colon tumor xenografts by targeted delivery of maytansinoids," Proceedings of the National Academy of Sciences, 1996, vol. 93, No. 16, pp. 8618-8623.

Lode et al., "Targeted Therapy with a Novel Enediyene Antibiotic Calicheamicin θ|1 Effectively Suppresses Growth and Dissemination of Liver Metastases in a Syngeneic Model of Murine Neuroblastoma," Cancer Research, 1998, vol. 58, pp. 2925-2928.

Luckow et al., "Trends in the Development of Baculovirus Expression Vectors," Bio/Technology, Jan. 1988, vol. 6, pp. 47-55.

Majeti et al., "CD47 is an adverse prognostic factor and therapeutic antibody target on human acute myeloid leukemia stem cells," Author manuscript, Cell, Jul. 23, 2009, vol. 138, No. 2, pp. 286-299, 24 pages.

Marks et al., "By-passing Immunization: Human Antibodies from V-gene Libraries Displayed on Phage," Journal of Molecular Biology, 1991, vol. 222, pp. 581-597.

Martinelli et al., "Anti-epidermal growth factor receptor monoclonal antibodies in cancer therapy," Clinical & Experimental Immunology, 2009, vol. 158, 9 pages.

McCafferty et al., "Phage antibodies: filamentous phage displaying antibody variable domains," Nature, Dec. 6, 1990, vol. 348, pp. 552-554.

Nedeljkovic et al., "Mechanisms of Chemotherapy Resistance in Triple-Negative Breast Cancer—How We Can Rise to the Challenge," Cells, 2019, vol. 8, No. 957, 32 pages.

Nigro et al., "Enhanced Expression of CD47 Is Associated With Off-Target Resistance to Tyrosine Kinase Inhibitor Gefitinib NSCLC," Frontiers in Immunology, Jan. 2020, vol. 10, No. 3135, 13 pages.

Oldenborg et al., "CD47-Signal Regulatory Protein a (SIRPα) Regulates Fcγ and Complement Receptor-mediated Phagocytosis," Journal of Experimental Medicine, Apr. 2, 2001, vol. 193, No. 7, pp. 855-861.

Ou et al., "Bioprocess development of antibody-drug conjugate production for cancer treatment," PLoS ONe, Oct. 23, 2018, vol. 13, No. 10, 14 pages.

Ou et al., "Novel biomanufacturing platform for large-scale and high-quality human T cells production," Journal of Biological Engineering, 2019, vol. 13, No. 34, 13 pages.

Polakis, Paul, "Antibody Drug Conjugates for Cancer Therapy," Pharmacological Reviews, Jan. 2016, vol. 68, pp. 3-19.

Presta et al., "Humanization of an Antibody Directed Against IgE," The Journal of Immunology, Sep. 1, 1993, vol. 151, No. 5, pp. 2623-2632.

Riechmann et al., "Reshaping human antibodies for therapy," Nature, vol. 332, Mar. 24, 1988, pp. 323-327.

Samanta et al., "Chemotherapy induces enrichment of CD47+/CD73+/PDL1+ immune evasive triple-negative breast cancer cells," PNAS, Jan. 24, 2018, pp. E1239-E1248.

Seaman et al., "Eradication of Tumors through Simultaneous Ablation of CD276/B7-H3 Positive Tumor Cells and Tumor Vasculature," Author manuscript, Cancer Cell, Apr. 10, 2017, vol. 31, No. 4, pp. 501-515, 44 pages.

Seligson et al., "Sacituzumab Govitecan-hziy: An Antibody-Drug Conjugate for the Treatment of Refractory, Metastatic, Tiple-Negative Breast Cancer," Annals of Pharmacotherapy, 2021, vol. 55, No. 7, pp. 921-931.

Sheets et al., "Efficient construction of a large nonimmune phage antibody library: The production of high-affinity human single-chain antibodies to protein antigens," Proceedings of the National Academy of Sciences USA, May 1998, vol. 95, pp. 6157-6162.

Shibata et al. "Targeting Cancer Stem Cells: A Strategy for Effective Eradication of Cancer," Cancers, 2019, vol. 11, No. 732, 18 pages.

Si et al., "Anti-CD47 Monoclonal Antibody-Drug Conjugate: A Targeted Therapy to Treat Triple-Negative Breast Cancers," Vaccines, 2021, vol. 9, No. 882, 14 pages.

Si et al., "Anti-EGFR antibody-drug conjugate for triple-negative breast cancer therapy," Engineering in Life Sciences, 2021, vol. 21, pp. 37-44.

Si et al., "Anti-SSTR2 antibody-drug conjugate for neuroendocrine tumor therapy," Cancer Gene Therapy, 2021, vol. 28, pp. 799-812.

Si et al., "Dual-Targeted Extracellular Vesicles to Facilitate Combined Therapies for Neuroendocrine Cancer Treatment," Pharmaceutics, Nov. 2020, vol. 12, No. 1079, 13 pages.

Silver et al., "Efficacy of Neoadjuvant Cisplatin in Triple-Negative Breast Cancer," Journal of Clinical Oncology, Mar. 1, 2010, vol. 28, No. 7, pp. 1145-1153.

Sims et al., "A Humanized CD18 Antibody Can Block Function without Cell Destruction," The Journal of Immunology, Aug. 15, 1993, vol. 151, No. 4, pp. 2296-2308.

Sissung et al., "Pharmacogenetics of Membrane Transporters: An Update on Current Approaches," Molecular Biotechnology, 2010, vol. 44, pp. 152-167.

Steinmetz et al., "Isolation, Crystal and Solution Structure Determination, and Biosynthesis of Tubulysins-Powerful Inhibitors of Tubulin Polymerization from Myxobacteria," Angewandte Chemie International Edition, 2004, vol. 43, pp. 4888-4892.

Vaughan et al., "Human Antibodies with Sub-nanomolar Affinities Isolated from a Large Non-immunized Phage Display Library," Nature Biotechnology, Mar. 1996, vol. 14, pp. 309-314.

Vaupel, Peter, "Hypoxia Aggressive Tumor Phenotype: Implications for Therapy and Prognosis," The Oncologist, 2008, vol. 13, Supp. 3, pp. 21-26.

Wahby et al., "FDA Approval Summary: Accelerated Approval of Sacituzumab Govitecan-hziy for Third-line Treatment of Metastatic Triple-negative Breast Cancer," Clinical Cancer Research, Apr. 1, 2021, vol. 27, No. 7, pp. 1850-1854.

Wein et al., "Mechanisms of resistance of chemotherapy in early-stage triple negative breast cancer (TNBC)," The Breast, 2017, vol. 34, pp. S27-S30.

Weiskopf et al., "CD47-blocking immunotherapies stimulate macrophage-mediated destruction of small-cell lung cancer," The Journal of Clinical Investigation, Jul. 2016, vol. 126, No. 7, pp. 2610-2620.

Weiskopf et al., "Engineered SIRPα variants as immunotherapeutic adjuvants to anti-cancer antibodies," Author manuscript, Science, Jul. 5, 2013, vol. 341, No. 6141, 13 pages.

Weiskopf, Kipp, "Cancer immunotherapy targeting the CD47/SIRPα axis," European Journal of Cancer, 2017, vol. 76, pp. 100-109.

Willingham et al., "The CD47-signal regulatory protein alpha (SIRPa) interaction is a therapeutic target for human solid tumors," PNAS, Apr. 24, 2012, vol. 109, No. 17, pp. 6662-6667.

Woyke et al., "Effect of Auristatin PHE on Microtubule Integrity and Nuclear Localization in Cryptococcus heoformans," Antimicrobial Agents and Chemotherapy, Dec. 2002, vol. 46, No. 12, pp. 3802-3808.

Xu et al., "Proteomics insight into the production of monoclonal antibody," Biochemical Engineering Journal, 2019, vol. 145, pp. 177-185.

Yamada et al., "High expression of ATP-binding cassette transporter ABCC11 in breast tumors is associated with aggressive subtypes and low disease-free survival," Breast Cancer Research and Treatment, 2013, vol. 137, pp. 773-782.

Zhang et al., "HIF-1 regulates CD47 expression in breast cancer cells to promote evasion of phagocytosis and maintenance of cancer stem cells," PNAS, Oct. 28, 2015, pp. E6215-E6223.

(56) References Cited

OTHER PUBLICATIONS

Zhang et al., "Hurdles of CAR-T cell-based cancer immunotherapy directed against solid tumors," Science China Life Sciences, Apr. 2016, vol. 59, No. 4, pp. 340-348.
Zhou et al., "Targeted biopharmaceuticals for cancer treatment," Cancer Letters, 2014, vol. 352, pp. 145-151.

* cited by examiner

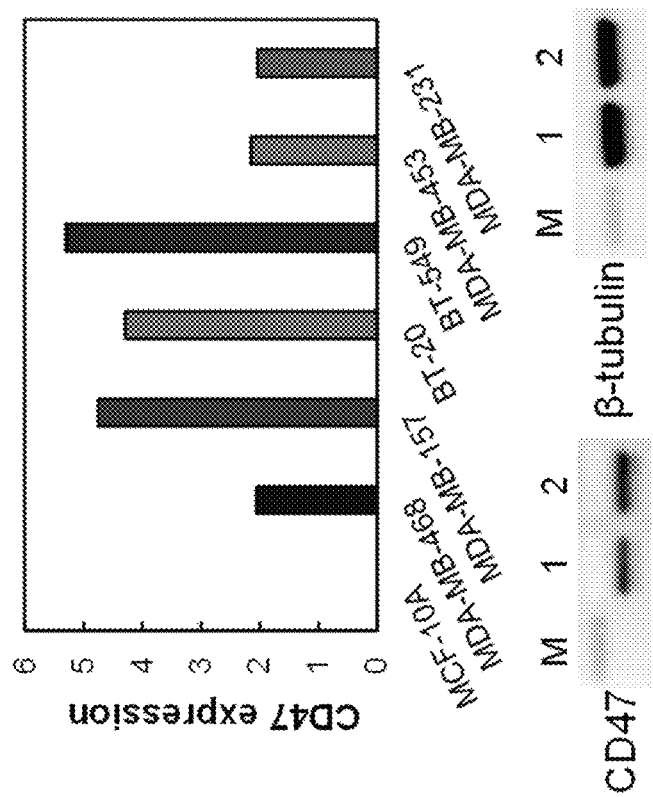
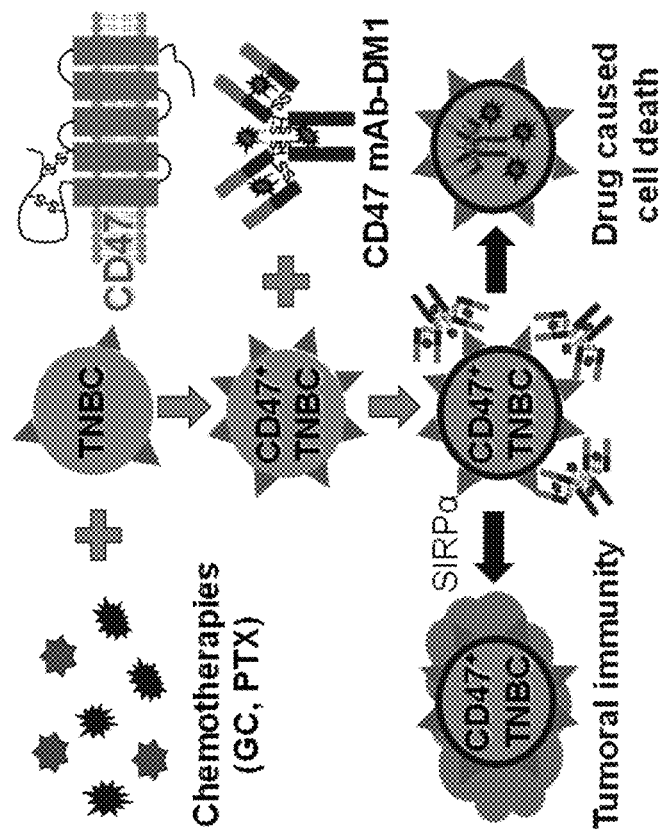
FIG. 1B
FIG. 1C
FIG. 1A

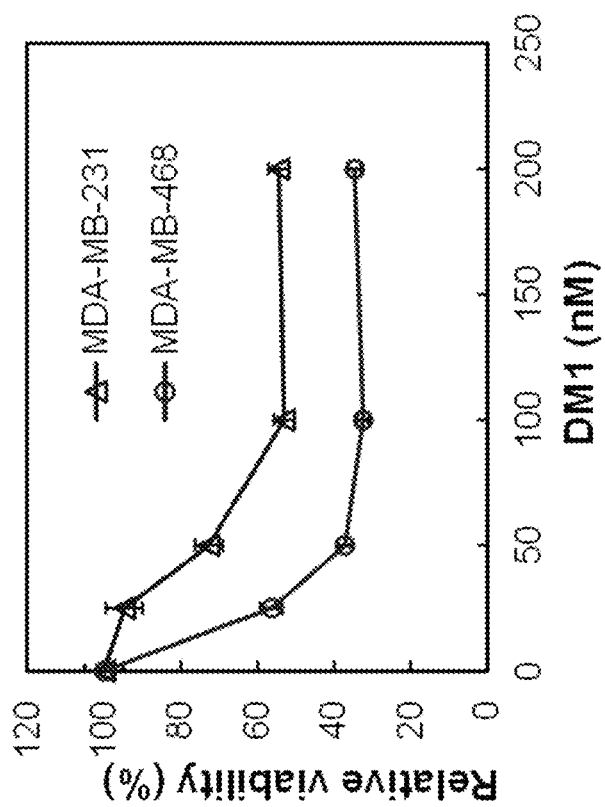
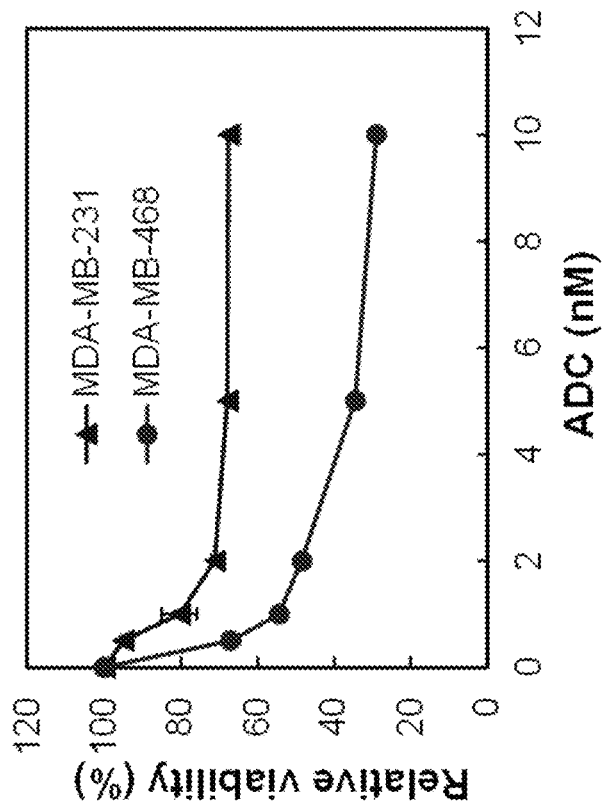
FIG. 5A
FIG. 5B

ANTI-CD47 ANTIBODY AND USES THEREOF

CROSS-REFERENCE TO RELATED APPLICATIONS

This application claims benefit of U.S. Provisional Application No. 63/229,807, filed Aug. 5, 2021, which is hereby incorporated herein by reference in its entirety.

SEQUENCE LISTING

This application contains a sequence listing filed in ST.26 format entitled "222119-1090 Sequence Listing" created on Aug. 4, 2022. The content of the sequence listing is incorporated herein in its entirety.

STATEMENT REGARDING FEDERALLY SPONSORED RESEARCH OR DEVELOPMENT

This invention was made with Government Support under Grant No. CA238273 and CA242917 awarded by the National Institutes of Health. The Government has certain rights in the invention.

BACKGROUND

The highly aggressive heterogeneous triple-negative breast cancers (TNBCs, HER2$^-$/ER$^-$/PR$^-$) account for 15-20% of breast cancers. The standard cytotoxic chemotherapies, e.g., anthracycline-taxane and gemcitabine (GC)-paclitaxel (Liedtke, C., et al. J Clin Oncol 2008, 26:1275-1281; Silver, D. P.; et al. J Clin Oncol 2010, 28:1145-1153; Nedeljkovic, M.; et al. Cells 2019, 8; Wein, L.; et al. Breast 2017, 34 Suppl 1:S27-S30), are currently the main systemic treatment options. However, TNBCs usually develop drug resistance and result in distant metastasis post primary treatment and chemotherapy, which could be caused by ATP-binding cassette transporters-mediated drug efflux (Sissung, T. M.; et al. Mol Biotechnol 2010, 44:152-167; Yamada, A.; et al. Breast Cancer Res Treat 2013, 137:773-782; Mahmood, N. A.; et al. Int J Mol Cell Med 2018, 7:234-240), cancer stem cells (Shibata, M.; et al. Cancers (Basel) 2019, 11; Khan, A. Q.; et al. Cells 2019, 8), hypoxia (Vaupel, P. et al. Oncologist 2008, 13 Suppl 3:21-26; Cosse, J. P.; et al. Anticancer Agents Med Chem 2008, 8:790-797), dysregulation of apoptosis (Inao, T.; et al. Oncotarget 2018, 9:25545-25556; Campbell, K. J.; et al. Cell Death Dis 2018, 9:19), heterogeneity (Lehmann, B. D.; et al. J Clin Invest 2011, 121:2750-2767; Lehmann, B. D.; et al. PLoS One 2016, 11:e0157368), activation of survival, growth and invasion signaling pathways (Lehmann, B. D.; et al. PLoS One 2016, 11:e0157368), or others (Nedeljkovic, M.; et al. Cells 2019, 8; Wein, L.; et al. Breast 2017, 34 Suppl 1:S27-S30). Moreover, the adverse effects, early relapse, high recurrence rate (>50%) and poor survival (Silver, D. P.; et al. J Clin Oncol 2010, 28:1145-1153; Nedeljkovic, M.; et al. Cells 2019, 8; Wein, L.; et al. Breast 2017, 34 Suppl 1:S27-S30; Mahmood, N. A.; et al. Int J Mol Cell Med 2018, 7:234-240) have significantly reduced the clinical benefits of chemotherapies (Al-Mahmood, S.; et al. Drug Deliv Trans) Res 2018, 8:1483-1507; Lebert, J. M.; et al. Curr Oncol 2018, 25:S142-S150). Thus, a targeted treatment strategy is needed for TNBC especially after standard therapies.

SUMMARY

Disclosed herein is an antibody that selectively binds CD47 on tumor cells. In some embodiments, the antibody has a variable heavy ($V_H$) domain having CDR1, CDR2 and CDR3 sequences and a variable light ($V_L$) domain having CDR1, CDR2 and CDR3 sequences, wherein the CDR1 sequence of the $V_H$ domain comprises the amino acid sequence FTFNTYAMN (SEQ ID NO:5), the CDR2 sequence of the $V_H$ domain comprises the amino acid sequence WIARIRSKSNNYATYY (SEQ ID NO:6), the CDR3 sequence of the $V_H$ domain comprises the amino acid sequence RPAQGAMDY (SEQ ID NO:7), the CDR1 sequence of the $V_L$ comprises the amino acid sequence QRISNNLH (SEQ ID NO:8), the CDR2 sequence of the $V_L$ domain comprises the amino acid sequence LLIKYSSQSIS (SEQ ID NO:9), and the CDR3 sequence of the $V_L$ domain comprises the amino acid sequence QQSNAWPY (SEQ ID NO:10).

In some embodiments, the $V_H$ domain comprises the amino acid sequence SEQ ID NO:3. In some embodiments, the $V_H$ domain has at least 90% sequence identity to the amino acid sequence SEQ ID NO:3. In some embodiments, the $V_L$ domain comprises the amino acid sequence SEQ ID NO:4. In some embodiments, the $V_L$ domain has at least 90% sequence identity to the amino acid sequence SEQ ID NO:4.

In some embodiments, the antibody is a monoclonal antibody. In some embodiments, the antibody is humanized. In some embodiments, the antibody is a chimeric antibody. In some embodiments, the antibody is conjugated to a cytotoxin to form an antibody-drug conjugate. In some embodiments, the cytotoxin is selected from the group consisting of an auristatin, a calicheamicin, a maytansinoid, or a tubulysin. In some embodiments, the cytotoxin is monomethylauristatin E, monomethylauristatin F, calicheamicin γ, mertansine, tubulysin T3, or tubulysin T4.

Also disclosed is a method for treating cancer in a subject, comprising administering to the subject an effective amount of the antibody disclosed herein.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A to 1O show surface receptor CD47 in TNBC. FIG. 1A shows mechanism to target CD47 with ADC. FIG. 1B shows relative expression of CD47 receptor in TNBC cells. FIG. 1O shows Western blotting analysis of CD47 in GC treated MDA-MB-231 cells.

FIG. 2A shows rank of top anti-CD47 mAb clones based on the titer in ELISA screening (data represent mean±SEM, n=3). FIG. 2B shows mAb production and hybridoma cell growth (data represent mean±SEM, n=3). Viable cell density (VCD): ▲, cell viability: ∆. FIG. 2C shows SDS-PAGE to confirm the integrity and purity of mAb and ADC. FIG. 2D shows HPLC to analyze the ADC synthesis efficiency.

FIG. 3A shows flow cytometry to analyze the surface binding of anti-CD47 mAb to TNBC cells (MDA-MB-231, MDA-MB-468 and 4T1) and negative control cell (184B5).

FIG. 3B shows live-cell confocal microscopy imaging of the internalization of anti-CD47 mAb in MDA-MB-468 cells. Cytoplasm labeled with GFP, nucleus labelled with NucBlue, and mAb-labeled with AF647. Scale bar equals 10 µm.

Figures 4A, 4B:
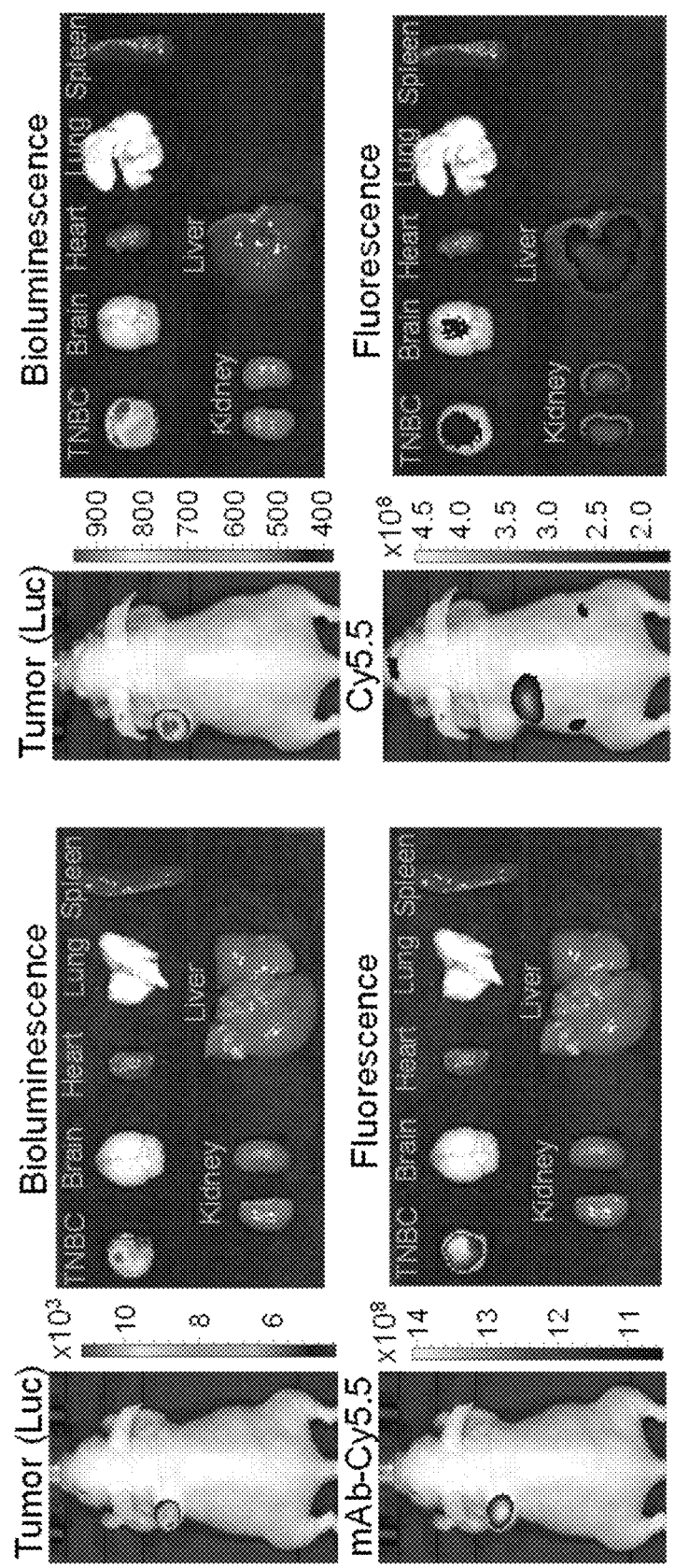

FIGS. 4A and 4B show in vivo TNBC targeting by anti-CD47 mAb in xenograft mice. FIG. 4A shows live-animal and ex vivo IVIS imaging to confirm TNBC-specific targeting of CD47 mAb-Cy5.5 at 24 hr post tail vein injection. FIG. 4B shows IVIS imaging showing the non-specific distribution of Cy5.5 dye.

FIGS. 5A and 5B show in vitro anti-TNBC cytotoxicity of anti-CD47 ADC (FIG. 5A) and free drug DM1 (FIG. 5B). ●: MDA-MB-468, and ▲: MDA-MB-231. Data represent mean±SEM, n=3.

Figure 6A:
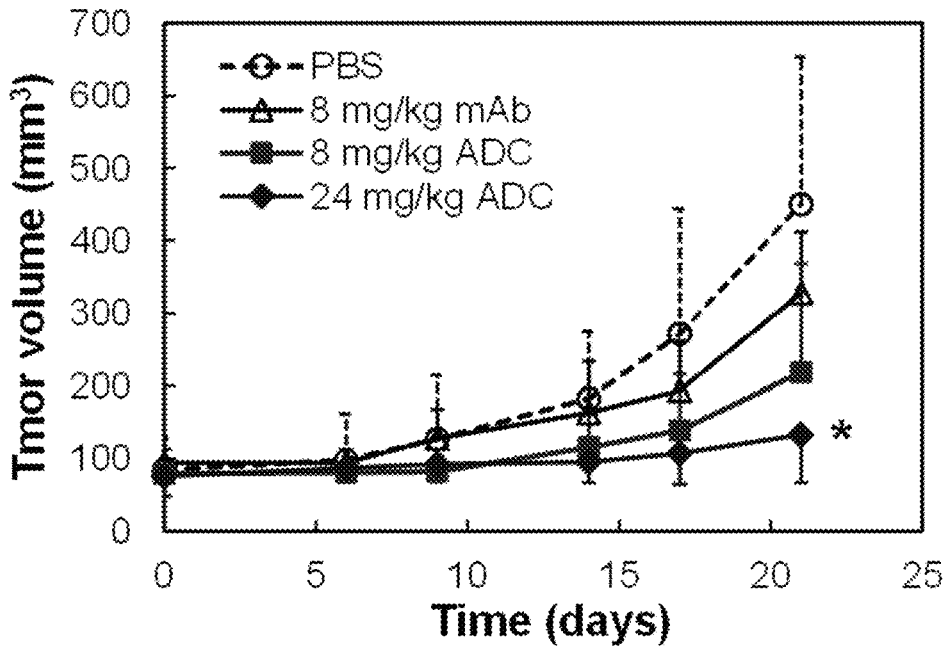
Figure 6B:
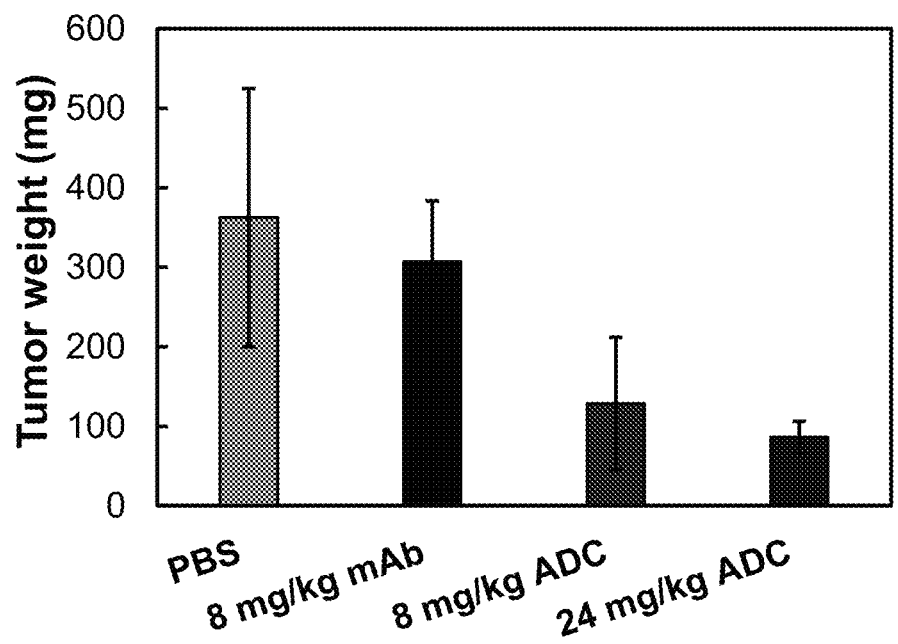
Figure 6C:
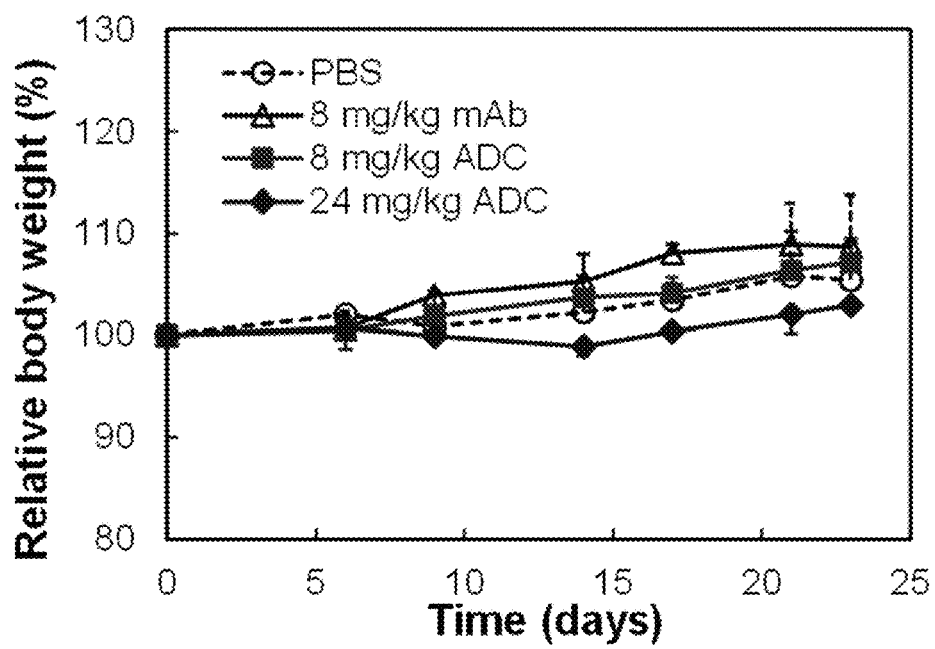
Figure 6D:
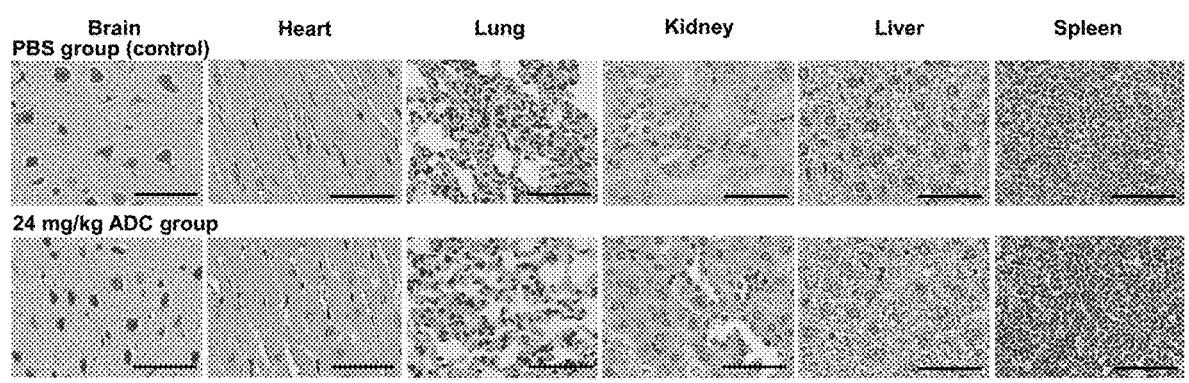

FIGS. 6A to 6D show anti-tumor efficacy study of ADC in TNBC (MDA-MB FLuc) xenografted NSG mouse models. FIG. 6A shows tumor volume changes with ADC treatment (data represent mean±SEM, n=5). PBS, mAb or ADC were i.v. administrated on Day 6, 10, 14 and 18. Tumor size was measured with a caliper. Tumor volumes between 4 groups were analyzed with mixed design ANOVA and multiple comparison. *$p<0.005$. FIG. 6B show wet weight of the tumors excised from euthanized mice. *$p≤0.005$. FIG. 6C shows body weight changes. ○: PBS, Δ: 8 mg/kg mAb, ■: 8 mg/kg ADC, and ◆: 24 mg/kg ADC. FIG. 6D shows H&E staining of main organs, including brain, heart, lung, kidney, liver and spleen. Scale bar equals to 50 µm.

Figure 7A:
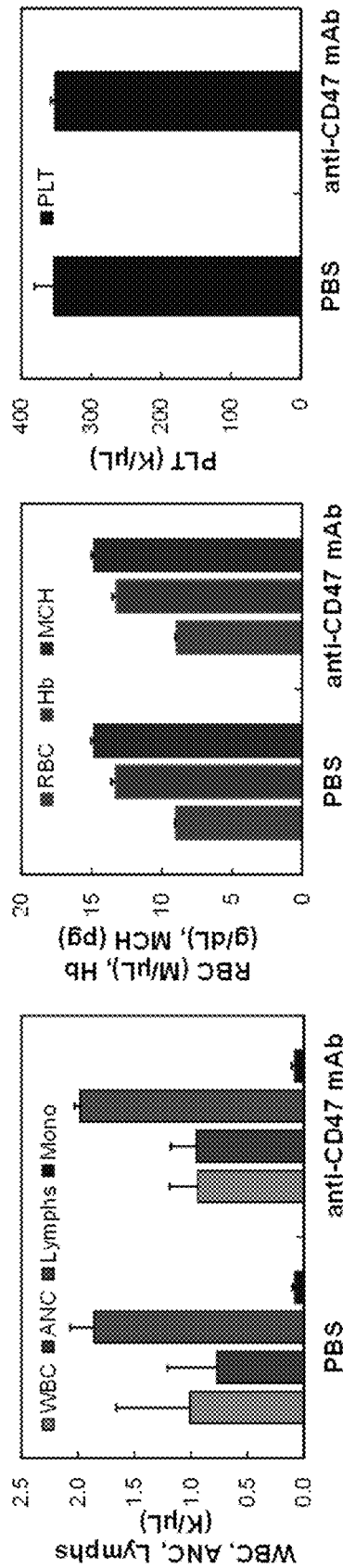
Figure 7B:
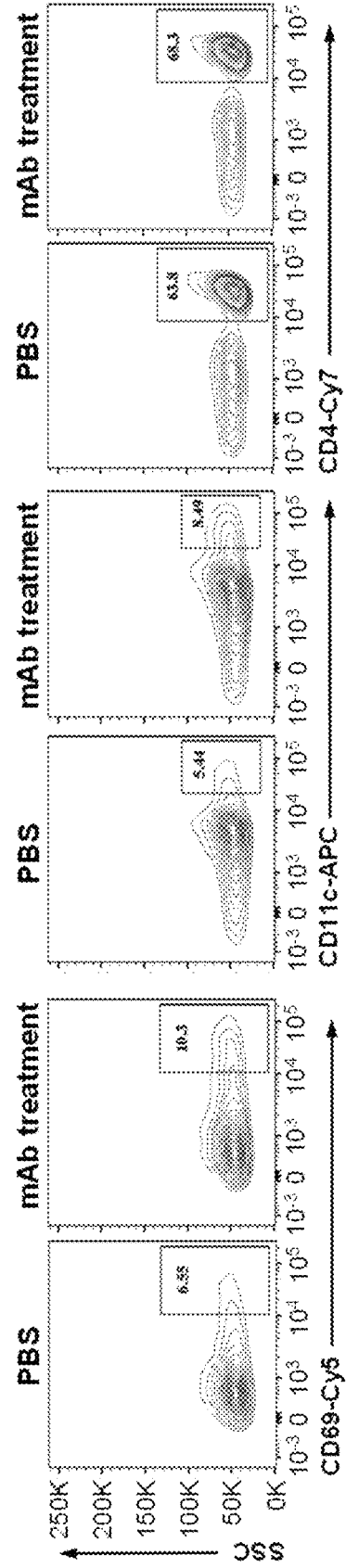

FIGS. 7A and 7B show immune response analysis. FIG. 7A shows whole blood analysis showing the effect of anti-CD47 mAb on peripheral immunity. FIG. 7B shows flow cytometry analysis of immune cells in lymph nodes.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, biology, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

The term "cytotoxic agent" as used herein is defined broadly and refers to a substance that inhibits or prevents the function of cells and/or causes destruction of cells (cell death), and/or exerts anti-neoplastic/anti-proliferative effects. For example, cytotoxic agent prevents directly or indirectly the development, maturation, or spread of neoplastic tumor cells. The term includes also such agents that cause a cytostatic effect only and not a mere cytotoxic effect. The term includes chemotherapeutic agents as specified below, anti-angiogenic agents, tyrosine kinase inhibitors, protein kinase A inhibitors, members of the cytokine family, radioactive isotopes, and toxins such as enzymatically active toxins of bacterial, fungal, plant or animal origin.

The term "chemotherapeutic agent" is a subset of the term "cytotoxic agent" comprising natural or synthetic chemical compounds. Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, *Vinca* alkaloids and derivatives of podophyllotoxin; cytotoxic antibiotics and camptothecin derivatives. Other chemotherapeutic agents are amifostine (ETHYOL®), cisplatin, dacarbazine (DTIC), dactinomycin, mechlorethamine (nitrogen mustard), streptozocin, cyclophosphamide, carrnustine (BCNU), lomustine (CCNU), doxorubicin (ADRIAMYCIN®), doxorubicin lipo (DOXIL®), gemcitabine (GEMZAR®), daunorubicin, daunorubicin lipo (DAUNOXOME®), procarbazine, mitomycin, cytarabine, etoposide, methotrexate, 5-fluorouracil (5-FU), vinblastine, vincristine, bleomycin, paclitaxel (TAXOL®), docetaxel (TAXOTERE®), aldesleukin, asparaginase, busulfan, carboplatin, cladribine, camptothecin, CPT-11, 10-hydroxy-7-ethyl-camptothecin (SN38), gefitinib (IRESSA 0), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil aromatase inhibitors, and combinations thereof.

The terms "antibody" or "immunoglobulin," as used interchangeably herein, include whole antibodies and any antigen binding fragment or single chains thereof and combinations thereof (e.g., bispecific antibodies).

A typical antibody comprises at least two heavy (H) chains and two light (L) chains interconnected by disulfide bonds. Each heavy chain is comprised of a heavy chain variable region (abbreviated herein as VH) and a heavy chain constant region (abbreviated herein as CH). The heavy chain constant region is comprised of three domains, CH1, CH2, and CH3. Each light chain is comprised of a light chain variable region (abbreviated herein as VL) and a light chain constant region. The light chain constant region is comprised of one domain, CL. The VH and VL regions can be further subdivided into regions of hypervariability, termed Complementarity Determining Regions (CDR), interspersed with regions that are more conserved, termed framework regions (FW). Each VH and VL is composed of three CDRs and four FWs, arranged from amino-terminus to carboxy-terminus in the following order: FW1, CDR1, FW2, CDR2, FW3, CDR3, FW4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system. Exemplary antibodies of the present disclosure include typical antibodies, scFvs, and combinations thereof where, for example, an scFv is covalently linked (for example, via peptidic bonds or via a chemical linker) to the N-terminus of either the heavy chain and/or the light chain of a typical antibody, or intercalated in the heavy chain and/or the light chain of a typical antibody.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain variable fragment (scFv), disulfide stabilized scFvs, multispecific antibodies such as bispecific antibodies generated from at least two intact antibodies and/or antigen binding fragments thereof, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity.

An antibody can be of any the five major classes of immunoglobulins: IgA, IgD, IgE, IgG, and IgM, or subclasses (isotypes) thereof (e.g. IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc. to form ADCs.

A "blocking" antibody or an "antagonist" antibody is one which inhibits or reduces biological activity of the antigen it binds, such as HER2. In a certain aspect, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The terms "anti-CD47 antibody" or "anti-CD47" refers to an antibody that is capable of binding CD47 with sufficient affinity such that the antibody is useful as a therapeutic agent or diagnostic reagent in targeting CD47. The extent of binding of an anti-CD47 antibody to an unrelated, non-CD47 protein is less than about 10% of the binding of the antibody to CD47 as measured, e.g., by a radioimmunoassay (RIA), or BIACORE™ (using recombinant CD47 as the analyte and antibody as the ligand, or vice versa), or other binding assays known in the art. In certain aspects, an antibody that binds to CD47 has a dissociation constant ($K_D$) of ≤1 µM, ≤100 nM, ≤10 nM, ≤1 nM, ≤0.1 nM, ≤10 pM, ≤1 pM, or ≤0.1 pM.

The terms "antigen binding fragment" refers to a portion of an intact antibody and refers to the antigenic determining variable regions of an intact antibody. It is known in the art that the antigen binding function of an antibody can be performed by fragments of a full-length antibody. Examples of antibody fragments include, but are not limited to Fab, Fab', F(ab')2, and Fv fragments, linear antibodies, single chain antibodies, and multispecific antibodies formed from antibody fragments.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants.

The term "monoclonal antibody" encompasses both intact and full-length monoclonal antibodies as well as antibody fragments (such as Fab, Fab', F(ab')2, Fv), single chain variable fragments (scFv), fusion proteins comprising an antibody portion, and any other modified immunoglobulin molecule comprising an antigen recognition site. Furthermore, "monoclonal antibody" refers to such antibodies made in any number of ways including, but not limited to, by hybridoma, phage selection, recombinant expression, and transgenic animals (e.g., expression of a human antibody in a transgenic mouse).

The term "humanized antibody" refers to an antibody derived from a non-human (e.g., murine) immunoglobulin, which has been engineered to contain minimal non-human (e.g., murine) sequences. Typically, humanized antibodies are human immunoglobulins in which residues from the CDRs are replaced by residues from the CDRs of a non-human species (e.g., mouse, rat, rabbit, or hamster) that have the desired specificity, affinity, and capability (Jones et al., 1986, Nature, 321:522-525; Riechmann et al., 1988, Nature, 332:323-327; Verhoeyen et al., 1988, Science, 239:1534-1536). In some instances, the FW residues of a human immunoglobulin are replaced with the corresponding residues in an antibody from a non-human species that has the desired specificity, and/or affinity, and/or capability.

The humanized antibody can be further modified by the substitution of additional residues either in the FW regions and/or within the replaced non-human residues to refine and optimize antibody specificity, and/or affinity, and/or capability. In general, the humanized antibody will comprise substantially all of at least one, and typically two or three, variable domains containing all or substantially all of the CDR regions that correspond to the non-human immunoglobulin whereas all or substantially all of the FW regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539 or 5,639,641.

A "variable region" of an antibody refers to the variable region of the antibody light chain or the variable region of the antibody heavy chain, either alone or in combination. The variable regions of the heavy and light chain each consist of four FW regions connected by three CDR regions. The CDRs in each chain are held together in close proximity by the FW regions and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, (5th ed., 1991, National Institutes of Health, Bethesda Md.)); and (2) an approach based on crystallographic studies of antigen-antibody complexes (Al-lazikani et al. (1997) J. Molec. Biol. 273:927-948)). In addition, combinations of these two approaches are sometimes used in the art to determine CDRs. The Kabat numbering system is generally used when referring to a residue in the variable domain (approximately residues 1-107 of the light chain and residues 1-113 of the heavy chain) (e.g., Kabat et al., Sequences of Immunological Interest, 5th Ed. Public Health Service, National Institutes of Health, Bethesda, Md. (1991)).

The term "chimeric antibodies" refers to antibodies wherein the amino acid sequence of the immunoglobulin molecule is derived from two or more animal species. Typically, the variable region of both light and heavy chains corresponds to the variable region of antibodies derived from one species of mammals (e.g., mouse, rat, rabbit, etc.) with the desired specificity, and/or affinity, and/or capability while the constant regions are homologous to the sequences in antibodies derived from another species (usually human) to avoid eliciting an immune response in that species.

"Antibody-dependent cell-mediated cytotoxicity" or "ADCC" refers to a form of cytotoxicity in which secreted immunoglobulins bound onto Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. Specific high-affinity IgG antibodies directed to the surface of target cells "arm" the cytotoxic cells and are absolutely required for such killing. Lysis of the target cell is extracellular, requires direct cell-to-cell contact, and does not involve complement. It is contemplated that, in addition to antibodies, other proteins comprising Fc regions, specifically Fc fusion proteins, having the capacity to bind specifically to an antigen-bearing target cell will be able to effect cell-mediated cytotoxicity. For simplicity, the cell-mediated cytotoxicity resulting from the activity of an Fc fusion protein is also referred to herein as ADCC activity.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cells or compositions include those which have been purified to a degree that they are no longer in a form in which they are found in nature. In some aspects, an antibody, polynucleotide, vector, cell, or composition which is isolated is substantially pure.

The term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

The term "pharmaceutical composition" refers to a preparation which is in such form as to permit the biological activity of the active ingredient (e.g., an anti-CD47 binding molecule disclosed herein) to be effective, and which contains no additional components which are unacceptably toxic to a subject to which the composition would be administered. Such composition can be sterile.

An "effective amount" of an anti-CD47 binding molecule as disclosed herein is an amount sufficient to carry out a specifically stated purpose. An "effective amount" can be determined empirically and in a routine manner, in relation to the stated purpose.

The term "therapeutically effective amount" refers to an amount of an anti-CD47 binding molecule disclosed herein or other drug effective to "treat" a disease or disorder in a subject or mammal.

Terms such as "treating" or "treatment" or "to treat" or "alleviating" or "to alleviate" refer to both (1) therapeutic measures that cure, slow down, lessen symptoms of, and/or halt progression of a diagnosed pathologic condition or disorder and (2) prophylactic or preventative measures that prevent and/or slow the development of a targeted pathologic condition or disorder. Thus, those in need of treatment include those already with the disorder; those prone to have the disorder; and those in whom the disorder is to be prevented. In certain aspects, a subject is successfully "treated" for cancer according to the methods of the present disclosure if the patient shows, e.g., total, partial, or transient remission of a certain type of cancer.

The terms "cancer", "tumor", "cancerous", and "malignant" refer to or describe the physiological condition in mammals that is typically characterized by unregulated cell growth. Examples of cancers include but are not limited to, carcinoma including adenocarcinomas, lymphomas, blastomas, melanomas, sarcomas, and leukemias. More particular examples of such cancers include squamous cell cancer, small-cell lung cancer, non-small cell lung cancer, gastrointestinal cancer, Hodgkin's and non-Hodgkin's lymphoma, pancreatic cancer, glioblastoma, glioma, cervical cancer, ovarian cancer, liver cancer such as hepatic carcinoma and hepatoma, bladder cancer, breast cancer (including hormonally mediated breast cancer, see, e.g., Innes et al. (2006) Br. J. Cancer 94:1057-1065), colon cancer, colorectal cancer, endometrial carcinoma, myeloma (such as multiple myeloma), salivary gland carcinoma, kidney cancer such as renal cell carcinoma and Wilms' tumors, basal cell carcinoma, melanoma, prostate cancer, vulval cancer, thyroid cancer, testicular cancer, esophageal cancer, various types of head and neck cancer and cancers of mucinous origins, such as, mucinous ovarian cancer, cholangiocarcinoma (liver) and renal papillary carcinoma. In some aspects, the term cancer as used herein specifically refers to cancer expressing CD47.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide can comprise modified nucleotides, such as methylated nucleotides and their analogs. The preceding description applies to all polynucleotides referred to herein, including RNA and DNA.

The term "vector" means a construct, which is capable of delivering, and in some aspects, expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of the instant disclosure are based upon antibodies, in certain aspects, the polypeptides can occur as single chains or associated chains.

A "recombinant" polypeptide or protein refers to a polypeptide or protein produced via recombinant DNA technology. Recombinantly produced polypeptides and proteins expressed in engineered host cells are considered isolated for the purpose of the invention, as are native or recombinant polypeptides which have been separated, fractionated, or partially or substantially purified by any suitable technique. The polypeptides disclosed herein can be recombinantly produced using methods known in the art. Alternatively, the proteins and peptides disclosed herein can be chemically synthesized.

A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, if an amino acid in a polypeptide is replaced with another amino acid from the same side chain family, the substitution is considered to be conservative. In another aspect, a string of amino acids can be conservatively replaced with a structurally similar string that differs in order and/or composition of side chain family members.

The term "percent sequence identity" between two polypeptide or polynucleotide sequences refers to the number of identical matched positions shared by the sequences over a comparison window, taking into account additions or deletions (i.e., gaps) that must be introduced for optimal alignment of the two sequences. A matched position is any position where an identical nucleotide or amino acid is presented in both the target and reference sequence. Gaps presented in the target sequence are not counted since gaps are not nucleotides or amino acids. Likewise, gaps presented in the reference sequence are not counted since target sequence nucleotides or amino acids are counted, not nucleotides or amino acids from the reference sequence. The percentage of sequence identity is calculated by determining the number of positions at which the identical amino-acid residue or nucleic acid base occurs in both sequences to yield the number of matched positions, dividing the number of matched positions by the total number of positions in the window of comparison and multiplying the result by 100 to yield the percentage of sequence identity. The comparison of sequences and determination of percent sequence identity between two sequences can be accomplished using readily available software both for online use and for download.

Suitable software programs are available from various sources, and for alignment of both protein and nucleotide sequences. One suitable program to determine percent sequence identity is bl2seq, part of the BLAST suite of program available from the U.S. government's National Center for Biotechnology Information BLAST web site (blast.ncbi.nlm.nih.gov). Bl2seq performs a comparison between two sequences using either the BLASTN or BLASTP algorithm. BLASTN is used to compare nucleic acid sequences, while BLASTP is used to compare amino acid sequences. Other suitable programs are, e.g., Needle, Stretcher, Water, or Matcher, part of the EMBOSS suite of bioinformatics programs and also available from the European Bioinformatics Institute (EBI).

Anti CD47 Antibody

The present disclosure provides anti-CD47 binding molecules, e.g., anti-CD47 antibodies or molecules comprising CD47-binding fragments thereof that specifically bind HER2.

In certain aspects, the anti-CD47 binding molecules are antibodies or antigen-binding fragments thereof. In some aspects, the anti-CD47 molecules, e.g., anti-CD47 antibodies or molecules comprising CD47-binding fragments thereof, comprise a Fab, a Fab', a F(ab')2, a Fd, a single chain Fv, scFv, disulfide stabilized scFv, a disulfide linked Fv, a V-NAR domain, an IgNar, an intrabody, an IgGΔCH2, a minibody, a F(ab')3, a tetrabody, a triabody, a diabody, a single-domain antibody, DVD-Ig, Fcab, mAb2, a (scFv)2, or a scFv-Fc. In some aspects, the antibody is of the IgG type, for example of the IgG1 type.

In some aspects, the anti-CD47 binding molecules are monospecific. In other aspects, the anti-CD47 binding molecules are bispecific, trispecific, tetraspecific, etc. In other aspects, the anti-CD47 binding molecules are multispecific. In some aspects, the anti-CD47 binding molecules are monovalent, bivalent, trivalent, tetravalent, etc. In yet other aspects, the anti-CD47 binding molecules are multivalent. In specific aspects, the anti-CD47 binding molecules are bivalent, e.g., an antibody comprising two CD47 specific antigen binding sites. In specific aspects, the anti-CD47 binding molecules are bispecific, i.e., the molecule can specifically bind to two different antigens (e.g., two different epitopes on the same or different molecules). In some specific aspects, the anti-CD47 binding molecules are bivalent and tetravalent, e.g., an antibody comprising four antigen-binding sites that are capable of binding to two different antigens (e.g., two different epitopes on the same or different molecules).

In some aspects, the anti-CD47 binding molecule of the instant disclosure (e.g., an anti-CD47 antibody or CD47-binding fragment thereof, or a bispecific anti-CD47 antibody) comprises a heavy chain constant region or fragment thereof. In some specific aspects, the heavy chain constant region is an IgG constant region. The IgG constant region can comprise a light chain constant region selected from the group consisting of a kappa constant region and a lambda constant region.

In some embodiments, the heavy chain of the anti-CD47 monoclonal antibody has the amino acid sequence (SEQ ID NO: 1)
MLLGLKWVFFVVFYQGVHCEVQLVESGGGLVQPKGSLKLSCAASGFTFNT

YAMNWVRQAPGKGLEWIARIRSKSNNYATYYADSMKDRFTISRDDSQSML

YLQMNNLKTEDTAMYYCVRPAQGAMDYWGHGTSVTVSSSKTTPPSVYPLA

PGCGDTTGSSVTLGCLVKGYFPESVTVTWNSGSLSSSVHTFPALLQSGLY

TMSSSVTVPSSTWPSQTVTCSVAHPASSTTVDKKLEPSGPISTINPCPPC

KECHKCPAPNLEGGPSVFIFPPNIKDVLMISLTPKVTCVVVDVSEDDPDV

QISWFVNNVEVHTAQTQTHREDYNSTIRVVSTLPIQHQDWMSGKEFKCKV

NNKDLPSPIERTISKIKGLVRAPQVYILPPPAEQLSRKDVSLTCLVVGFN

PGDISVEWTSNGHTEENYKDTAPVLDSDGSYFIYSKLNMKTSKWEKTDSF

SCNVRHEGLKNYYLKKSFSRTPGK.

In some embodiments, the light chain of the anti-CD47 monoclonal antibody has the amino acid sequence (SEQ ID NO: 2)
MVFTPQILGLMLFWISASRGDIVLTQSPATLSVTPGDSVSLSCRASQRIS

NNLHWYQQKSHESPRLLIKYSSQSISGIPSRFSGSGSGTDFTLSINSVET

EDFGMYFCQQSNAWPYTFGGGTKLEIRRADAAPTVSIFPPSSEQLTSGGA

SVVCFLNNFYPKDINVKWKIDGSERQNGVLNSWTDQDSKDSTYSMSSTLT

LTKDEYERHNSYTCEATHKTSTSPIVKSFNRNEC.

In some embodiments, the anti-CD47 monoclonal antibody comprises a variable heavy ($V_H$) domain having CDR1, CDR2 and CDR3 sequences and a variable light ($V_L$) domain having CDR1, CDR2 and CDR3 sequences. For example, in some embodiments, the $V_H$ domain has the amino acid sequence EVQLVESGGGLVQPKGSLKLS-CAASGFTFNTYAMNWVRQAPGKGLEWIARIR-SKSNN YATYYADSMKDRFTISRDDSQSM-LYLQMNNLKTEDTAMYYCVRPAQGAMDYWGHGT SVTVSS (SEQ ID NO:3). In some embodiments, the $V_L$ domain has the amino acid sequence (SEQ ID NO: 4)
DIVLTQSPATLSVTPGDSVSLSCRASQRISNNLHWYQQKSHESPRLLIKY

SSQSISGIPSRFSGSGSGTDFTLSINSVETEDFGMYFCQQSNAWPYTFGG

GTKLEIRR.

In some embodiments, the CDR1 sequence of the $V_H$ domain comprises the amino acid sequence FTFNTYAMN (SEQ ID NO:5), the CDR2 sequence of the $V_H$ domain comprises the amino acid sequence WIARIRSKSN-NYATYY (SEQ ID NO:6), the CDR3 sequence of the $V_H$ domain comprises the amino acid sequence RPAQGAMDY (SEQ ID NO:7), the CDR1 sequence of the $V_L$ comprises the amino acid sequence QRISNNLH (SEQ ID NO:8), the CDR2 sequence of the $V_L$ domain comprises the amino acid sequence LLIKYSSQSIS (SEQ ID NO:9), and the CDR3 sequence of the $V_L$ domain comprises the amino acid sequence QQSNAWPY (SEQ ID NO:10).

In other aspects, the $V_H$ and/or $V_L$ amino acid sequences can be 85%, 90%, 95%, 96%, 97%, 98% or 99% similar to the sequences set forth above, and comprise 1, 2, 3, 4, 5 or more conservative substitutions. An anti-CD47 binding molecule disclosed herein having $V_H$ and/or $V_L$ regions having high (i.e., 80% or greater) similarity to the $V_H$ region of SEQ ID NO:3 and/or $V_L$ region of SEQ ID NO:4, respectively, can be obtained by mutagenesis (e.g., site-directed or PCR-mediated mutagenesis) of their respective encoding nucleic acid molecules, followed by testing of the altered antibody for retained function using the functional assays described herein.

In certain aspects, an anti-CD47 binding molecule of the instant disclosure can specifically bind CD47 with a dissociation constant or $k_d$ ($k_{off}/k_{on}$) of less than $10^{-6}$ M, or of less than $10^{-7}$ M, or of less than $10^{-8}$ M, or of less than $10^{-9}$ M, or of less than $10^{-10}$ M, or of less than $10^{-11}$ M, or of less than $10^{-12}$ M, or of less than $10^{-13}$ M.

The affinity and/or avidity of an anti-CD47 binding molecule disclosed herein for an antigen can be determined experimentally using any suitable method well known in the art, e.g., flow cytometry, enzyme-linked immunosorbent assay (ELISA), or radioimmunoassay (RIA), or kinetics (e.g., BIACORE™ analysis). Direct binding assays as well as competitive binding assay formats can also be readily employed. See, for example, Berzofsky et al., "Antibody-Antigen Interactions," In Fundamental Immunology, Paul, W. E., Ed., Raven Press: New York, N.Y. (1984); Kuby, Immunology, W. H. Freeman and Company: New York, N.Y. (1992); and methods described herein.

The measured affinity of the interaction of a particular anti-CD47 binding molecule disclosed herein with a CD47 antigen can vary if measured under different conditions (e.g., salt concentration, pH, temperature). Thus, measurements of affinity and other antigen-binding parameters (e.g., $K_D$ or $K_d$, $k_{on}$, $k_{off}$) are made with standardized solutions of anti-CD47 binding molecule and antigen, and a standardized buffer, as known in the art and such as the buffer described herein.

It also known in the art that affinities measured using BIACORE™ analysis can vary depending on which one of the reactants is bound to the chip. In this respect, affinity can be measured using a format in which the targeting anti-CD47 binding molecule is immobilized onto the chip (referred to as an "IgG down" format) or using a format in which the target protein (e.g., CD47) is immobilized onto the chip.

Antibody-Drug Conjugates

Antibody-drug conjugate (ADC) molecules disclosed herein comprise at least one of the anti-CD47 binding molecules disclosed derivatized or linked (e.g., chemically or recombinantly) to another molecule (e.g., a peptide, small drug molecule, detectable molecule, etc.). In general, anti-CD47 antibodies or portions thereof are derivatized such that their CD47 binding is not affected adversely by the derivatization or labeling. Accordingly, the anti-CD47 antibodies and antibody portions of the instant disclosure are intended to include both intact and modified forms of the anti-CD47 binding molecules described herein. For example, an anti-CD47 binding molecule disclosed herein or CD47-binding portion thereof can be functionally linked (by chemical coupling, genetic fusion, noncovalent association, or otherwise) to one or more other molecular entities, such as a cytotoxic agent, a pharmaceutical agent, a detection agent, and/or a protein or peptide that can mediate association of the anti-CD47 binding molecule with another molecule (such as a streptavidin core region or a polyhistidine tag).

One type of derivatized molecule can be produced by crosslinking two or more molecular entities, e.g., an anti-CD47 binding molecule disclosed herein and a therapeutic moiety (e.g., a cytotoxin). Suitable crosslinkers include those that are heterobifunctional, i.e., having two distinctly reactive groups separated by an appropriate spacer (e.g., m-maleimidobenzoyl-N-hydroxysuccinimide ester); or homobifunctional (e.g., disuccinimidyl suberate). Such crosslinkers are available, for example, from Pierce Chemical Company, Rockford, Il. Additional bifunctional coupling agents include N-succinimidyl-3-(2-pyridyldithiol) propionate (SPDP), succinimidyl-4-(N-maleimidomethyl) cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene).

Another type of derivatized molecule can be produced by incorporating a detectable label. Useful detection agents include fluorescent compounds (e.g., fluorescein, fluorescein isothiocyanate, rhodamine, 5-dimethylamine napthalenesulfonyl chloride, phycoerythrin, lanthanide phosphors and the like), enzymes that are useful for detection (e.g., horseradish peroxidase, β-galactosidase, luciferase, alkaline phosphatase, glucose oxidase and the like), epitopes recognized by a secondary reporter (e.g., leucine zipper pair sequences, binding sites for secondary antibodies, metal binding domains, epitope tags, etc.). In some aspects, detectable labels can be attached by at least one spacer arm. Spacer arms can be of various lengths to reduce potential steric hindrance.

An anti-CD47 binding molecule can also be labeled with a radiolabeled amino acid. The radiolabel can be used for both diagnostic and therapeutic purposes. For instance, the radiolabel can be used to detect CD47-expressing cells by X-ray or other diagnostic techniques such as positron emission tomography (PET).

Further, the radiolabel can be used therapeutically as a toxin for CD47-expressing cells, such as those which cause unwanted immune response. Examples of labels for polypeptides include, but are not limited to, the following radioisotopes or radionuclides: $^{3}$H, $^{14}$C, $^{15}$N, $^{35}$S, $^{90}$Y, $^{99}$Tc, $^{111}$In, $^{125}$I and $^{131}$I. In some aspects, the anti-HER2 binding molecule can be labeled with a paramagnetic, radioactive, or fluorogenic ion that is detectable upon imaging. In some aspects, the paramagnetic ion is chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) or erbium (III). In other aspects, the radioactive ion is iodine-123, technetium-99, indium-111, rhenium-188, rhenium-186, copper-67, iodine-131, yttrium-90, iodine-125, astatine-211, and gallium-67. In other aspects, the anti-HER2 binding molecule is labeled with an X-ray imaging agent such as lanthanum (III), gold (III), lead (II), and bismuth (III). An anti-HER2 binding molecule can also be derivatized with a chemical group, for example a polymer such as polyethylene glycol (PEG), a methyl group, an ethyl group, or a carbohydrate group. These groups are useful to improve the biological characteristics of the antibody, e.g., to increase serum half-life or to increase tissue binding.

In some aspects, the ADC comprises an anti-CD47 binding molecule disclosed herein conjugated to one or more tubulysin molecules. Tubulysins are members of a class of natural products isolated from myxobacterial species (Sasse et al., J. Antibiot. 53:879-885 (2000)). As cytoskeleton interacting agents, tubulysins are mitotic poisons that inhibit tubulin polymerization and lead to cell cycle arrest and apoptosis (Steinmetz et al., Chem. Int. Ed. 43:4888-4892 (2004); Khalil et al., ChemBioChem. 7:678-683 (2006); Kaur et al., Biochem. J. 396: 235-242 (2006)). Tubulysins are extremely potent cytotoxic molecules, exceeding the cell growth inhibition of any clinically relevant traditional chemotherapeutic, e.g., epothilones, paclitaxel, and vinblastine. Furthermore, they are potent against multidrug resistant cell lines (Domling et al., Mol. Diversity 9:141-147 (2005)). These compounds show high cytotoxicity tested against a panel of cancer cell lines with 1050 values in the low picomolar range; thus, they are of interest as anticancer therapeutics. See, e.g., WO2012019123, which is herein incorporated by reference in its entirety. Tubulysin conjugates are disclosed, e.g., in U.S. Pat. No. 7,776,814.

In some aspects, the ADC comprises an anti-CD47 binding molecule disclosed herein conjugated to one or more maytansinoid molecules. Maytansinoids are mitotic inhibitors which act by inhibiting tubulin polymerization. Examples of maytansinoids include Ansamitocin, Mertansine/emtansine (DM1), and Ravtansine/soravtansine (DM4). Maytansine was first isolated from the east African shrub Maytenus serrata (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533. Maytansinoid drug moieties are attractive drug moieties in antibody drug conjugates because they are: (i) relatively accessible to prepare by fermentation or chemical modification, derivatization of fermentation products, (ii) amenable to derivatization with functional groups suitable for conjugation through the non-disulfide linkers to antibodies, (iii) stable in plasma, and (iv) effective against a variety of tumor cell lines. Immunoconjugates containing maytansinoids, methods of making same, and their therapeutic use are disclosed, for example, in U.S. Pat. Nos. 5,208,020, 5,416,064 and European Patent EP0425235B1; Liu et al., Proc. Natl. Acad. Sci. USA 93:8618-8623 (1996) (described immunoconjugates comprising a maytansinoid designated DM1); and Chari et al., Cancer Research 52:127-131 (1992).

Antibody-maytansinoid conjugates are prepared by chemically linking an antibody to a maytansinoid molecule without significantly diminishing the biological activity of either the antibody or the maytansinoid molecule. See, e.g., U.S. Pat. No. 5,208,020. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020.

In some aspects, the ADC comprises an anti-CD47 binding molecule disclosed herein conjugated to dolastatins or dolostatin peptidic analogs and derivatives, the auristatins (U.S. Pat. Nos. 5,635,483; 5,780,588). Dolastatins and auristatins have been shown to interfere with microtubule dynamics, GTP hydrolysis, and nuclear and cellular division (Woyke et al., Antimicrob. Agents and Chemother. 45:3580-3584 (2001)) and have anticancer activity (U.S. Pat. No. 5,663,149). The dolastatin or auristatin drug moiety can be attached to the antibody through the N (amino) terminus or the C (carboxyl) terminus of the peptidic drug moiety (See, e.g., WO2002088172).

In some aspects, the ADC comprises an anti-CD47 binding molecule disclosed herein conjugated to one or more calicheamicin molecules. Members of the calicheamicin family of antibiotics are capable of producing double-stranded DNA breaks at sub-picomolar concentrations. The calicheamicins are a class of enediyne antibiotics derived from the bacterium *Micromonospora echinospora*, with calicheamicin γ1 being the most notable. Other calicheamicins are β1Br, γ1Br, α2I, α3I, β1I, γ1I, and Δ1I. See Lee et al., Journal of Antibiotics 42(7):1070-87 (1989). For the preparation of conjugates of the calicheamicin family, see U.S. Pat. Nos. 5,712,374, 5,714,586, 5,739,116, 5,767,285, 5,770,701, 5,770,710, 5,773,001, 5,877,296. Structural analogues of calicheamicin which can be used include, but are not limited to, γ1I, α2I, α3I, N-acetyl-γ1I, PSAG and θ1I (Hinman et al., Cancer Research 53:3336-3342 (1993), Lode et al., Cancer Research 58:2925-2928 (1998) and the aforementioned U.S. patents to American Cyanamid).

In some aspects, the ADC comprises an anti-CD47 binding molecule disclosed herein conjugated to one or more duocarmycin molecules. Duocarmycins are members of a series of related natural products first isolated from *Streptomyces* bacteria and they are potent antitumor antibiotics. See Boger. (1991). Chemtracts: Organic Chemistry 4 (5): 329-349 (1991); Tercel et al., Chem. Int. Ed. Engl. 52(21): 5442-6 (2013); Boger & Douglas, Proc. Natl. Acad. Sci. USA 92(9): 3642-3649 (1995); Cacciari et al., Expert Opinion on Therapeutic Patents 10(12):1853-71 (2000). Natural duocarmycins include duocarmycin A, duocarmycin B 1, duocarmycin B2, duocarmycin C1, duocarmycin C2, duocarmycin D, duocarmycin SA, and CC-1065. Synthetic analogs include adozelesin, bizelesin, and carzelesin (U-80244).

In some aspects, the cytotoxic drug is a pyrrolobenzodiazepine (PBD). PBDs are relatively small molecules and some have the ability to recognize and covalently bind to specific sequences in the minor groove of DNA and thus exhibit antibiotic/antitumor activity. A number of PBDs and derivatives thereof are known in the art, for example, PBD dimers (e.g., SJG-136 or SG2000), 02-unsaturated PBD dimers, pyrrolobenzodiazepine dimers bearing C2 aryl substitutions (e.g., SG2285), PBD dimer pro-drug that is activated by hydrolysis (e.g., SG2285), and polypyrrole-PBD (e.g., SG2274). PBDs are further described WO 2000/012507, WO 2007/039752, WO 2005/110423, WO 2005/085251, and WO 2005/040170, and U.S. Pat. No. 7,612,062, each of which is incorporated by reference herein in its entirety.

Other cytotoxic drugs include BCNU, anthracyclines (e.g., daunomycin or adriamycin), taxenes (e.g., paclitaxel), streptozoicin, *Vinca* alkaloids (e.g., vincristine), 5-fluorouracil, the family of agents known collectively as LL-E33288 complex (see U.S. Pat. Nos. 5,053,394, and 5,770,710), esperamicins (see U.S. Pat. No. 5,877,296). The ADC can also comprise an anti-HER2 binding molecule disclosed herein (e.g., the 39S antibody or a derivative thereof, or one of the bispecific anti-HER2 antibodies disclosed herein) conjugated to enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Saponaria officinalis* inhibitor, gelonin, mitogellin, restrictocin, phenomycin, enomycin and the tricothecenes. See, for example, WO199321232. In some aspects, the cytotoxic agent is a light activated drug.

Preparation of Anti-CD47 Binding Molecules

Anti-CD47 binding molecules of the present disclosure can be prepared according to methods known in the art. For example, anti-CD47 binding molecules can be generated using hybridoma methods, such as those described by Kohler & Milstein (1975) Nature 256:495.

Using the hybridoma method, a mouse, hamster, or other appropriate host animal, is immunized as described above to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g. radioimmunoassay (RIA); enzyme-linked immunosorbent assay (ELISA)) can then be propagated either in in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

Anti-CD47 binding molecules of the present disclosure can also be made using recombinant DNA methods as described in U.S. Pat. No. 4,816,567. The polynucleotides encoding a monoclonal antibody are isolated from mature B-cells or hybridoma cell, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant anti-CD47 monoclonal antibodies or molecules comprising antigen-binding fragments thereof of the desired species can be isolated from phage display libraries expressing CDRs of the desired species as described (McCafferty et al., Nature 348:552-554 (1990); Clarkson et al., Nature 352:624-628 (1991); and Marks et al., J. Mol. Biol. 222: 581-597 (1991)).

The polynucleotide(s) encoding an anti-CD47 binding molecule of the present disclosure can further be modified in a number of different manners using recombinant DNA technology to generate alternative anti-CD47 binding molecules. In some aspects, the constant domains of the light and heavy chains of, for example, a mouse monoclonal antibody can be substituted (1) for those regions of, for example, a human antibody to generate a chimeric antibody or (2) for a non-immunoglobulin polypeptide to generate a fusion antibody. In some aspects, the constant regions are truncated or removed to generate the desired antibody fragment of a monoclonal antibody. Site-directed or high-density mutagenesis of the variable region can be used to optimize specificity, affinity, etc. of a monoclonal antibody.

In certain aspects, the anti-CD47 binding molecule of the present disclosure is a human antibody or antigen-binding fragment thereof. Human antibodies can be directly prepared using various techniques known in the art. Immortalized human B lymphocytes immunized in vitro or isolated from an immunized individual that produce an antibody directed against a target antigen can be generated (See, e.g., Cole et al., Monoclonal Antibodies and Cancer Therapy, Alan R. Liss, p. 77 (1985); Boemer et al., J. Immunol. 147:86-95 (1991); and U.S. Pat. No. 5,750,373). One or more cDNAs encoding the antibody in the immortalized B lymphocyte can then be prepared and inserted into an expression vector and/or a heterologous host cell for expression of a non-naturally-occurring recombinant version of the antibody.

Also, the anti-CD47 human antibody or antigen-binding fragment thereof can be selected from a phage library, where that phage library expresses human antibodies or fragments thereof as fusion proteins with heterologous phage proteins, as described, for example, in Vaughan et al., Nat. Biotech. 14:309-314 (1996); Sheets et al., Proc. Natl. Acad. Sci. 95:6157-6162 (1998); Hoogenboom and Winter, J. Mol. Biol. 227:381 (1991), and Marks et al., J. Mol. Biol. 222:581 (1991)). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963, each of which is incorporated by reference in its entirety.

Affinity maturation strategies and chain shuffling strategies (Marks et al., BioTechnology 10:779-783 (1992), incorporated by reference in its entirety) are known in the art and can be employed to generate high affinity human antibodies or antigen-binding fragments thereof.

In some aspects, an anti-CD47 binding molecule of the present disclosure can be a humanized antibody. Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence. Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing HER2 binding. Accordingly, part or all of the non-human or human CDR sequences are maintained while the non-human sequences of the variable and constant regions can be replaced with human or other amino acids. In certain aspects, human CDRs are inserted into non-human antibody scaffolds to make an antibody with reduced immunogenicity in an animal model system, e.g., a "murinized" antibody.

Anti-CD47 binding molecules, e.g., antibodies, can optionally be humanized, resurfaced, or engineered with retention of high affinity for the antigen CD47 and other favorable biological properties. To achieve this goal, humanized (or human) or engineered anti-CD47 antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art.

Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen, such as CD47. In this way, framework residues can be selected and combined from the consensus and import sequences so that the desired antibody characteristic, such as increased affinity for the target antigen(s), is achieved.

Humanization, resurfacing or engineering of the anti-CD47 binding molecules disclosed herein can be performed using any known method, such as but not limited to those described in, Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, 7,557,189; 7,538,195; and 7,342,110; WO90/14443; WO90/14424; WO90/14430; and EP229246, each of which is entirely incorporated herein by reference, including the references cited therein.

In certain aspects an anti-CD47 antibody fragment is provided. Various techniques are known for the production of antibody fragments. Traditionally, these fragments are derived via proteolytic digestion of intact antibodies (for example Morimoto et al., J. Biochem. Biophy. Methods 24:107-117 (1993); Brennan et al., Science, 229:81 (1985)). In certain aspects, anti-CD47 antibody fragments are produced recombinantly. Fab, Fv, and scFv antibody fragments can all be expressed in and secreted from E. coli or other host cells, thus allowing the production of large amounts of these fragments. Such anti-CD47 antibody fragments can also be isolated from the antibody phage libraries discussed above. The anti-CD47 antibody fragments can also be linear antibodies as described in U.S. Pat. No. 5,641,870. Other techniques for the production of antibody fragments will be apparent to the skilled practitioner.

Techniques can be adapted for the production of single-chain antibodies specific to the same CD47 epitope. In addition, methods can be adapted for the construction of Fab expression libraries (see, e.g., Huse et al., Science 246:1275-1281 (1989)) to allow rapid and effective identification of monoclonal Fab fragments with the desired specificity for CD47, or derivatives, fragments, analogs or homologs thereof. Antibody fragments can be produced by techniques in the art including, but not limited to: (a) a F(ab')2 fragment produced by pepsin digestion of an antibody molecule; (b) a Fab fragment generated by reducing the disulfide bridges of an F(ab')2 fragment, (c) a Fab fragment generated by the treatment of the antibody molecule with papain and a reducing agent, and (d) Fv fragments.

In some aspects, especially in the case of antibody fragments, an anti-CD47 antibody or antigen-binding fragment thereof can be modified in order to increase its serum half-life. This can be achieved, for example, by incorporation of a salvage receptor binding epitope into the antibody or antibody fragment by mutation of the appropriate region in the antibody or antibody fragment or by incorporating the epitope into a peptide tag that is then fused to the antibody or antibody fragment at either end or in the middle (e.g., by DNA or peptide synthesis), or by YTE mutation. Other methods to increase the serum half-life of an antibody or antigen-binding fragment thereof, e.g., conjugation to a heterologous molecule such as PEG are well known in the art.

Heteroconjugate anti-CD47 binding molecules can be prepared using recombinant biology technology as well as in vitro using known methods in synthetic protein chemistry, including those involving crosslinking agents. For example, bispecific antibodies or ADCs can be chemically constructed using a disulfide exchange reaction or by forming a thioether bond. Suitable reagents for this purpose are known in the art, and include iminothiolate and methyl-4-mercaptobutyrimidate.

It will be noted that in certain aspects, the anti-CD47 binding molecules can be engineered to fuse the CH3 domain directly to the hinge region of the respective modified antibodies or fragments thereof. In other constructs, a peptide spacer can be inserted between the hinge region and the modified CH2 and/or CH3 domains. For example, compatible constructs can be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain aspects, any spacer added to the construct will be relatively non-immunogenic, or even omitted altogether, so as to maintain the desired biochemical qualities of the modified antibodies.

Besides the deletion of whole constant region domains, it will be appreciated that the anti-CD47 binding molecule can be provided by the partial deletion or substitution of a few or even a single amino acid. For example, the mutation of a single amino acid in selected areas of the CH2 domain can be enough to substantially reduce Fc binding and thereby increase tumor localization. Moreover, as alluded to above, the constant regions of the disclosed anti-HER2 binding molecule can be modified through the mutation or substitution of one or more amino acids that enhances the profile of the resulting construct. In this respect it is possible to disrupt the activity provided by a conserved binding site (e.g., Fc binding) while substantially maintaining the configuration and immunogenic profile of the modified antibody or antigen-binding fragment thereof. Certain aspects can comprise the addition of one or more amino acids to the constant region to enhance desirable characteristics such as decreasing or increasing effector function or provide for more cytotoxin or carbohydrate attachment. In such aspects, specific sequences derived from selected constant region domains can be inserted or replicated.

Polynucleotides Encoding HER2-Binding Molecules

In certain aspects, the present disclosure provides polynucleotides comprising nucleic acid sequences that encode an anti-CD47 binding molecule disclosed herein that specifically binds CD47. For example, the instant disclosure provides a polynucleotide comprising a nucleic acid sequence that encodes an anti-CD47 binding molecule such as an antibody or a fragment thereof. The polynucleotides of the instant disclosure can be in the form of RNA or in the form of DNA. DNA includes cDNA, genomic DNA, and synthetic DNA; and can be double-stranded or single-stranded, and if single stranded can be the coding strand or non-coding (anti-sense) strand. In certain aspects the DNA is a cDNA that is used to produce a non-naturally-occurring recombinant antibody.

In certain aspects, the polynucleotides are isolated. In certain aspects, the polynucleotides are substantially pure. In certain aspects the polynucleotides comprise the coding sequence for the mature polypeptide fused in the same reading frame to a polynucleotide (either natural or heterologous) which aids, for example, in expression and secretion of a polypeptide from a host cell (e.g., a leader sequence which functions as a secretory sequence for controlling transport of a polypeptide from the cell). The polypeptide having a leader sequence is a preprotein and can have the leader sequence cleaved by the host cell to form the mature form of the polypeptide. The polynucleotides can also encode for an anti-CD47 binding molecule proprotein which is the mature protein plus additional 5' amino acid residues. In certain aspects, the polynucleotides are altered to optimize codon usage for a certain host cell.

In certain aspects the polynucleotides comprise the coding sequence for the mature anti-CD47 binding molecule, e.g., an anti-CD47 antibody or an antigen-binding fragment thereof fused in the same reading frame to a heterologous marker sequence that allows, for example, for purification of the encoded polypeptide. For example, the marker sequence can be a hexa-histidine (His6) tag supplied, for example, by a pQE-9 vector to provide for purification of the mature polypeptide fused to the marker in the case of a bacterial host. In other aspects, the marker sequence can be a hemagglutinin (HA) tag derived, for example, from the influenza hemagglutinin protein, when a mammalian host (e.g., COS-7 cells) is used.

The present disclosure further relates to variants of the described polynucleotides encoding, for example, CD47-binding fragments, analogs, and derivatives of the anti-CD47 binding molecules of the present disclosure.

The polynucleotide variants can contain alterations in the coding regions, non-coding regions, or both. In some aspects the polynucleotide variants contain alterations which produce silent substitutions, additions, or deletions, but do not alter the properties or activities of the encoded polypeptide. In some aspects, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*). Vectors and cells comprising the polynucleotides described herein are also provided.

In some aspects a DNA sequence encoding an anti-HER2 binding molecule, e.g., an anti-HER2 antibody or an antigen-binding fragment thereof can be constructed by chemical synthesis, for example, using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed, for example, by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain aspects, recombinant expression vectors are used to amplify and express DNA encoding anti-CD47 binding molecules. Recombinant expression vectors are replicable DNA constructs which have synthetic or cDNA-derived DNA fragments encoding, for example, a polypeptide chain of an anti-CD47 antibody or and antigen-binding fragment thereof, operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription.

The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *E. coli*, including pCR 1, pBR322, pMB9 and their derivatives, wider host range plasmids, such as M13 and filamentous single-stranded DNA phages.

Suitable host cells for expression of anti-CD47 binding molecules, e.g., anti-HER2 antibodies or antigen-binding fragments thereof, include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Additional information regarding methods of protein production, including antibody production, can be found, e.g., in U.S. Publ. No. 2008/0187954, U.S. Pat. Nos. 6,413,746 and 6,660,501, and Intl Pat. Publ. No. WO 04009823, each of which is hereby incorporated by reference in its entirety.

Various mammalian or insect cell culture systems can also be advantageously employed to express recombinant anti-CD47 binding molecules, e.g., anti-CD47 antibodies or antigen-binding fragments thereof. Expression of recombinant proteins in mammalian cells can be performed because such proteins are generally correctly folded, appropriately modified and completely functional. Examples of suitable mammalian host cell lines include HEK-293 and HEK-293T, the COS-7 lines of monkey kidney cells, described by Gluzman (Cell 23:175, 1981), and other cell lines including, for example, L cells, C127, 3T3, Chinese hamster ovary (CHO), NSO, HeLa, and BHK cell lines. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow & Summers, BioTechnology 6:47 (1988).

Anti-CD47 binding molecules, e.g., anti-CD47 antibodies or antigen-binding fragments thereof, produced by a transformed host can be purified according to any suitable method. Such standard methods include, for example, chromatography (e.g., ion exchange, affinity and sizing column chromatography), centrifugation, differential solubility, or by any other standard technique for protein purification. Affinity tags such as hexahistidine, maltose binding domain, influenza coat sequence, glutathione-S-transferase, etc., can be attached to the protein to allow easy purification by passage over an appropriate affinity column. Isolated proteins can also be physically characterized using, for example, proteolysis, nuclear magnetic resonance or x-ray crystallography.

For example, supernatants from systems which secrete recombinant protein into culture media can be first concentrated using a commercially available protein concentration filter, for example, an AMICON® or Millipore PELLICON® ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed.

Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify an HER2-binding molecule. Some or all of the foregoing purification steps, in various combinations, can also be employed to provide a homogeneous recombinant protein.

A recombinant anti-CD47 binding molecule, e.g., an anti-CD47 antibody or antigen-binding fragment thereof, produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Pat. Publ. Nos. US20080312425, US20080177048, and US20090187005, each of which is hereby incorporated by reference in its entirety.

Methods of Treatment

The present disclosure also provides methods directed to the use of anti-CD47 binding molecules, e.g., antibodies, including antigen-binding fragments, variants, and derivatives thereof, to treat patients having a disease associated with CD47 expression or CD47-expressing cells.

By "CD47-expressing cell" is meant a cell expressing the CD47 protein. Methods for detecting and/or quantitating CD47 expression in cells are well known in the art and include, but are not limited to, PCR techniques, immunohistochemistry (e.g., HERCEPTEST™), flow cytometry, Western blot, ELISA, and the like. In some aspects, the methods disclosed herein are applied to treatment and diagnostic method where the cancer cells are expressing CD47 at low levels.

The methods for diagnosis and treatment of various diseases and disorders with an anti-CD47 binding molecule disclosed herein, refer to anti-CD47 antibodies that retain the desired properties of the anti-CD47 binding molecules of the instant disclosure, e.g., capable of specifically binding CD47.

In one aspect, treatment includes the application or administration of an anti-CD47 binding molecule, e.g., an antibody or antigen binding fragment, variant, or derivative thereof of the current disclosure to a subject or patient, or application or administration of the anti-CD47 binding molecule to an isolated tissue or cell line from a subject or patient, where the subject or patient has a disease, a symptom of a disease, or a predisposition toward a disease. In another aspect, treatment is also intended to include the application or administration of a pharmaceutical composition comprising the anti-CD47 binding molecule, e.g., an antibody or antigen binding fragment, variant, or derivative thereof of the current disclosure to a subject or patient, or application or administration of a pharmaceutical composition comprising the anti-CD47 binding molecule to an isolated tissue or cell line from a subject or patient, who has a disease, a symptom of a disease, or a predisposition toward a disease.

The anti-CD47 binding molecules, e.g., antibodies or antigen-binding fragments, variants, or derivatives thereof of the present disclosure are useful for the treatment of various cancers. In one aspect, the instant disclosure relates to anti-CD47 binding molecules, e.g., antibodies or antigen-binding fragments, variants, or derivatives thereof for use as a medicament, in particular for use in the treatment or prophylaxis of cancer. Examples of cancer include, but are not limited to breast cancer, colon cancer, lung cancer, gastric cancer, head and neck squamous cells cancer, melanoma, pancreatic cancer, or prostate cancer. In some embodiments, the cancer is a triple negative breast cancer (TNBC).

In accordance with the methods of the present disclosure, at least one anti-CD47 binding molecule, e.g., an antibody or antigen binding fragment, variant, or derivative thereof as defined elsewhere herein is used to promote a positive therapeutic response with respect to cancer. The term "positive therapeutic response" with respect to cancer treatment refers to an improvement in the disease in association with the activity of these anti-CD47 binding molecules, e.g., antibodies or antigen-binding fragments, variants, or derivatives thereof, and/or an improvement in the symptoms associated with the disease.

For example, an improvement in the disease can be characterized as a complete response. The term "complete response" refers to an absence of clinically detectable disease with normalization of any previously test results. Alternatively, an improvement in the disease can be categorized as being a partial response. A "positive therapeutic response" encompasses a reduction or inhibition of the progression and/or duration of cancer, the reduction or amelioration of the severity of cancer, and/or the amelioration of one or more symptoms thereof resulting from the administration of an anti-CD47 binding molecule of the instant disclosure.

Clinical response can be assessed using screening techniques such as PET, magnetic resonance imaging (MRI) scan, x-radiographic imaging, computed tomographic (CT) scan, flow cytometry or fluorescence-activated cell sorter (FACS) analysis, histology, gross pathology, and blood chemistry, including but not limited to changes detectable by ELISA, RIA, chromatography, and the like. In addition to these positive therapeutic responses, the subject undergoing therapy with the anti-HER2 binding molecule, e.g., an antibody or antigen-binding fragment, variant, or derivative thereof, can experience the beneficial effect of an improvement in the symptoms associated with the disease.

The anti-CD47 binding molecules, e.g., antibodies or antigen-binding fragments, variants, or derivatives thereof of the instant disclosure can be used in combination with any known therapies for cancer, including any agent or combination of agents that are known to be useful, or which have been used or are currently in use, for treatment of cancer, e.g., colon cancer, lung cancer, gastric cancer, head and neck squamous cells cancer, and breast cancer. The second agent or combination of agents of the pharmaceutical combination formulation or dosing regimen preferably has complementary activities to anti-CD47 binding molecule(s) of the instant disclosure such that they do not adversely affect each other.

Anticancer agents include drugs used to treat malignancies, such as cancerous growths. Drug therapy can be used alone, or in combination with other treatments such as surgery or radiation therapy. Several classes of drugs can be used in cancer treatment, depending on the nature of the organ involved. For example, breast cancers are commonly stimulated by estrogens, and can be treated with drugs which inactive the sex hormones. Similarly, prostate cancer can be treated with drugs that inactivate androgens, the male sex hormone.

Anti-cancer agents for use in certain methods of the present disclosure include, among others, antibodies, small molecules targeting IGF1R, small molecules targeting EGFR, small molecules targeting HER2, antimetabolites, alkylating agents, topoisomerase inhibitors, microtubule targeting agents, kinase inhibitors, protein synthesis inhibitors, immunotherapeutic agents, hormonal therapies, glucocorticoids, aromatase inhibitors, mTOR inhibitors, chemotherapeutic agents, protein kinase B inhibitors, phosphatidylinositol 3-kinase (PI3K) inhibitors, cyclin dependent kinase (CDK) inhibitors, RLr9, CD289, enzyme inhibitors, anti-TRAIL, MEK inhibitors, etc.

In specific aspects, the anti-CD47 binding molecules disclosed herein, e.g., antibodies or antigen-binding fragments thereof, can be administered in combination with other antibodies or antibody fragments targeting epidermal growth factor receptor (EGFR), e.g. Erbitux® (cetuximab) or panitumumab (VECTIBIX®).

In other aspects, the anti-CD47 binding molecules disclosed herein can be administered in combination with kinase inhibitors, e.g., tyrosine kinase inhibitors. In some other specific aspects, the anti-CD47 binding molecules disclosed herein can be administered in combination with inhibitors of the tyrosine kinase activity associated with EGFR and/or HER2/neu, e.g., lapatinib. In some aspects, the anti-CD47 binding molecules of the instant disclosure can be administered in combination with antimitotic agents. In some specific aspects, the anti-CD47 binding molecules of the instant disclosure can be administered in combination with agents that stabilize the mitotic spindle microtubule assembly, e.g., paclitaxel or docetaxel.

Where the combined therapies comprise administration of an anti-CD47 binding molecule in combination with administration of another therapeutic agent, the methods of the instant disclosure encompass co-administration, using separate formulations or a single pharmaceutical formulation, and consecutive administration in either order. In some aspects, the anti-CD47 binding molecules described herein are administered in combination with other drugs, wherein the antibody or antigen-binding fragment, variant, or derivative thereof and the therapeutic agent(s) can be administered sequentially, in either order, or simultaneously (i.e., concurrently or within the same time frame).

The combination therapy can provide "synergy" and prove "synergistic", i.e., the effect achieved when the active ingredients used together is greater than the sum of the effects that results from using the compounds separately. A synergistic effect can be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect can be attained when the compounds are administered or delivered sequentially, e.g., by different injections in separate syringes. In general, during alternation therapy, an effective dosage of each active ingredient is administered sequentially, i.e., serially, whereas in combination therapy, effective dosages of two or more active ingredients are administered together.

In some aspects, the anti-CD47 binding molecule, e.g., an anti-CD47 antibody or antigen binding fragment thereof of the instant disclosure, can be administered in a synergistic combination with a growth factor receptor (EGFR) inhibitor. In some aspects, the EGFR inhibitor is an antibody. In specific aspects, the EGFR inhibitor antibody is ERBITUX® (cetuximab) or VECTIBIX® (panitumumab). In specific aspects, the anti-HER2 binding molecules of the instant disclosure, e.g., antibodies or antigen-binding fragments thereof, can be administered in a synergistic combination with inhibitors of the tyrosine kinase activity associated with EGFR and/or HER2/neu, e.g., lapatinib. In some aspects, the anti-CD47 binding molecules of the instant disclosure can be administered in a synergistic combination with an antimitotic agent. In some specific aspects the antimitotic agent stabilizes the mitotic spindle microtubule assembly. In some specific aspects, the antimitotic agent is paclitaxel or docetaxel.

A further aspect is the use of anti-CD47 binding molecules of the instant disclosure, e.g., antibodies or antigen-binding fragments, variants, or derivatives thereof, for diagnostic monitoring of protein levels in tissue as part of a clinical testing procedure, e.g., to determine the efficacy of a given treatment regimen. For example, detection can be facilitated by coupling the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 35S, or 3H.

Pharmaceutical Compositions and Administration Methods

Methods of preparing and administering anti-CD47 binding molecules, e.g., antibodies, or antigen-binding fragments, variants, or derivatives thereof, to a subject in need thereof are well known to or are readily determined by those skilled in the art. The route of administration of the anti-CD47 binding molecule, e.g., antibody, or antigen-binding fragment, variant, or derivative thereof can be, e.g., oral, parenteral, by inhalation or topical. The term parenteral as used herein includes, e.g., intravenous, intraarterial, intraperitoneal, intramuscular, subcutaneous, rectal, or vaginal administration. However, in other methods compatible with the teachings herein, anti-CD47 binding molecules, e.g., antibodies, or antigen-binding fragments, variants, or derivatives thereof of the instant disclosure can be delivered directly to the site of the adverse cellular population thereby increasing the exposure of the diseased tissue to the therapeutic agent.

As discussed herein, anti-CD47 binding molecules of the instant disclosure, e.g., antibodies, or antigen-binding fragments, variants, or derivatives thereof can be administered in a pharmaceutically effective amount for the in vivo treatment of CD47-expressing cell-mediated diseases such as certain types of cancers. The pharmaceutical compositions can comprise pharmaceutically acceptable carriers, including, e.g., water, ion exchangers, proteins, buffer substances, and salts. Preservatives and other additives can also be present. The carrier can be a solvent or dispersion medium. Suitable formulations for use in the therapeutic methods disclosed herein are described in Remington's Pharmaceutical Sciences (Mack Publishing Co.) 16th ed. (1980).

In any case, sterile injectable solutions can be prepared by incorporating an active compound (e.g., an anti-CD47 antibody, or antigen-binding fragment, variant, or derivative thereof by itself or in combination with other active agents) in the required amount in an appropriate solvent followed by filtered sterilization. Further, the preparations can be packaged and sold in the form of a kit. Such articles of manufacture can have labels or package inserts indicating that the associated compositions are useful for treating a subject suffering from, or predisposed to a disease or disorder.

Parenteral formulations can be a single bolus dose, an infusion or a loading bolus dose followed with a maintenance dose. These compositions can be administered at specific fixed or variable intervals, e.g., once a day, or on an "as needed" basis.

The composition can be administered as a single dose, multiple doses or over an established period of time in an infusion. Dosage regimens also can be adjusted to provide the optimum desired response (e.g., a therapeutic or prophylactic response).

Therapeutically effective doses of the compositions of the present disclosure, for treatment of CD47-expressing cell-mediated diseases such as certain types of cancers including e.g., colon cancer, lung cancer, gastric cancer, head and neck squamous cells cancer, melanoma, pancreatic cancer, prostate cancer, and breast cancer, vary depending upon many different factors, including means of administration, target site, physiological state of the patient, whether the patient is human or an animal, other medications administered, and whether treatment is prophylactic or therapeutic. In some specific aspects, the cancer expresses high levels of CD47 as determined. Usually, the patient is a human, but non-human mammals including transgenic mammals can also be treated. Treatment dosages can be titrated using routine methods known to those of skill in the art to optimize safety and efficacy.

The amount of at least one anti-CD47 binding molecule, e.g., antibody or binding fragment, variant, or derivative thereof to be administered can be readily determined by one of ordinary skill in the art without undue experimentation. Factors influencing the mode of administration and the respective amount of at least one anti-CD47 binding molecule, e.g., antibody, antigen-binding fragment, variant or derivative thereof include, but are not limited to, the severity of the disease, the history of the disease, and the age, height, weight, health, and physical condition of the individual undergoing therapy. Similarly, the amount of anti-CD47 binding molecule, e.g., antibody, or fragment, variant, or derivative thereof to be administered will be dependent upon the mode of administration and whether the subject will undergo a single dose or multiple doses of this agent.

The present disclosure also provides for the use of an anti-CD47 binding molecule, e.g., an antibody or antigen-binding fragment, variant, or derivative thereof in the manufacture of a medicament for treating a type of cancer, including, e.g., breast cancer, colon cancer, lung cancer, gastric cancer, head and neck squamous cells cancer, melanoma, pancreatic cancer, and prostate cancer. In some specific aspects, the cancer expresses high levels of CD47 as determined.

The disclosure also provides for the use of an anti-CD47 binding molecule, e.g., antibody of the instant disclosure, or antigen-binding fragment, variant, or derivative thereof, in the manufacture of a medicament for treating a subject for treating a type of cancer. In certain aspects, the medicament is used in a subject that has been pretreated with at least one other therapy.

By "pretreated" or "pretreatment" is intended the subject has received one or more other therapies (e.g., been treated with at least one other anti-cancer therapy) prior to receiving the medicament comprising the anti-CD47 binding molecule, e.g., antibody or antigen-binding fragment, variant, or derivative thereof. It is not necessary that the subject was a responder to pretreatment with the prior therapy or therapies. Thus, the subject that receives the medicament comprising the anti-CD47 binding molecule, e.g., an antibody or antigen-binding fragment, variant, or derivative thereof could have responded, responded poorly, or could have failed to respond to pretreatment with the prior therapy, or to one or more of the prior therapies where pretreatment comprised multiple therapies. Accordingly, the present disclosure provides methods to treat patients that are poor responders or non-responders to other therapies comprising administering an anti-CD47 binding molecule disclosed herein, e.g., an antibody or binding fragment, a variant, or a derivative thereof. Also provided are methods to prevent resistance to cancer therapies comprising administering an anti-CD47 binding molecule disclosed herein, e.g., an antibody or binding fragment, a variant, or a derivative thereof.

The present disclosure provides also methods to treat patients that are, for example, poor-responders or non-responders to another therapy. In cases where it is assessed that the subject is a "non-responder," a "poor-responder" or is "less likely to respond" (based, for example, on the presence of certain biomarkers in the cancer cells), the subject could be treated with the anti-CD47 binding molecules disclosed herein, e.g., antibody of the disclosure, or antigen-binding fragment, variant, or derivative thereof.

The instant disclosure also provides for the co-administration of an anti-HER2 binding molecule, e.g., antibody of the disclosure, or antigen-binding fragment, variant, or derivative thereof, and at least one other therapy. The anti-CD47 binding molecule and the at least one other therapy can be co-administered together in a single composition or can be co-administered together at the same time or overlapping times in separate compositions. In some aspects, an anti-CD47 binding molecule, e.g., antibody of the disclosure, or antigen-binding fragment, variant, or derivative thereof can be used as an adjuvant therapy.

The instant disclosure also provides for the use of an anti-CD47 binding molecule, e.g., antibody of the disclosure, or antigen-binding fragment, variant, or derivative thereof in the manufacture of a medicament for treating a subject for treating cancer, wherein the anti-CD47 binding molecule is administered before a subject has been treated with at least one other therapy.

Kits Comprising Anti-HER2 Binding Molecules

The present disclosure also provides kits that comprise an anti-CD47 binding molecule disclosed herein, e.g., an anti-CD47 antibody or antigen binding fragment thereof, that can be used to perform the methods described herein. In certain aspects, a kit comprises at least one purified anti-CD47 binding molecule or an antigen-binding fragment thereof in one or more containers. In some aspects, the kits contain all of the components necessary and/or sufficient to perform a detection assay, including all controls, directions for performing assays, and any necessary software for analysis and presentation of results. One skilled in the art will readily recognize that the disclosed anti-CD47 binding molecules disclosed herein, e.g., an anti-CD47 antibody or antigen binding fragment thereof, can be readily incorporated into one of the established kit formats which are well known in the art.

A number of embodiments of the invention have been described. Nevertheless, it will be understood that various modifications may be made without departing from the spirit and scope of the invention. Accordingly, other embodiments are within the scope of the following claims.

EXAMPLE

Anti-CD47 Monoclonal Antibody: A Targeted Therapy to Treat Triple-Negative Breast Cancers Introduction The CD47 receptor is highly expressed on tumor cells and provides a "don't eat me" signal via interacting with the N-terminus of signal regulatory protein alpha (SIRPα) on macrophages and other myeloid cells (Weiskopf, K. Eur J Cancer 2017, 76:100-109; Huang, Y.; et al. J Thorac Dis 2017, 9:E168-E174) to block phagocytosis (Kershaw, M. H.; Science 2013, 341:41-42; Gardai, S. J.; et al. Cell 2005, 123:321-334). Disrupting CD47-SIRPα ligand promotes the phagocytosis of tumor cells (Oldenborg, P. A.; et al. J Exp Med 2001, 193:855-862) and immunity-mediated antitumor effects (Liu, X.; et al. Nat Med 2015, 21:1209-1215; Weiskopf, K.; et al. J Clin Invest 2016, 126:2610-2620; Majeti, R.; et al. Cell 2009, 138:286-299; Chao, M. P.; et al. Cell 2010, 142:699-713; Willingham, S. B.; et al. Proc Natl Acad Sci USA 2012, 109: 6662-6667; Weiskopf, K.; et al. Science 2013, 341:88-91) (FIG. 1A). Furthermore, literature reported that the surface expression of glycoprotein CD47 in TNBC can be upregulated by chemotherapies (carboplatin, doxorubicin, GC and paclitaxel) (Samanta, D.; et al. Proc Natl Acad Sci USA 2018, 115:E1239-E1248; Nigro, A.; et al. Front Immunol 2019, 10:3135), but is not detectable or low in important organs or normal breast tissues (Willingham, S. B.; et al. Proc Natl Acad Sci USA 2012, 109: 6662-6667; Zhang, H.; et al. Proc Natl Acad Sci USA 2015, 112:E6215-6223). GC-resistant TNBC cells also had higher CD47 expression than drug-sensitive TNBCs. All these studies indicated that CD47 is an ideal target to treat drug-resistant or chemotherapy-treated TNBCs.

Targeted monoclonal antibodies (mAbs) and antibody-drug conjugates (ADCs) have been developed to treat various solid tumors (Zhou, L.; et al. Cancer Lett 2014, 352: 145-151; Almasbak, H.; et al. J Immunol Res 2016, 5474602; Dai, H.; et al. J Natl Cancer Inst 2016, 108; Magee, M. S.; et al. Discov Med 2014, 18:265-271; Zhang, B. L.; et al. Sci China Life Sci 2016, 59:340-348; Kunert, R.; et al. Appl Microbiol Biotechnol 2016, 100:3451-3461; Polakis, P. Pharmacol Rev 2016, 68:3-19; Si, Y.; et al. Cancer Gene Therapy. Cancer Gene Therapy 2020). The mAbs targeting epidermal growth factor receptor (EGFR) (Martinelli, E.; et al. Clin Exp Immunol 2009, 158:1-9; Flynn, J. F.; et al. J Oncol 2009, 526963) and folate receptor (Cheung, A.; et al. Clin Cancer Res 2018, 24:5098-5111; Frontera, E. D.; et al. Breast Cancer Res Treat 2018, 172:551-560) have been developed and evaluated for TNBC treatment, but their anti-tumor efficacy is poor in clinical trials. Recently the FDA approved the combination of Atezolizumab (immunotherapy) and Abraxane (chemotherapy) as a therapy to treat PD-L1$^+$ TNBC and the Sacituzumab govitecan (ADC) to treat trophoblast cell-surface antigen 2 (Trop-2)$^+$ TNBC (Bardia, A et al. N Engl J Med 2021, 384:1529-1541; Bardia, A.; et al. N Engl J Med 2019, 380:741-751; McGuinness, J. E.; et al. Expert Opin Biol Ther 2020; Seligson, J. M.; et al. Ann Pharmacother 2021, 55:921-931; Wahby, S.; et al. Clin Cancer Res 2021, 27:1850-1854). Combining the cancer specificity of antibody and high cytotoxicity of chemotherapy, ADCs have been investigated by us and others (Seaman, S.; et al. Cancer Cell 2017, 31:501-515 e508; Si, Y.; et al. Eng Life Sci 2021, 21:37-44). Despite this progress, drug resistance and high recurrence in TNBC patients remain challenging.

The objective of this study was to develop an innovative targeted ADC to treat TNBCs post chemotherapy. An anti-CD47 mAb (IgG2b/kappa) that targets the extracellular domain (Gln19-Glu141) of the cell surface receptor CD47 was developed. The ADC was constructed by conjugating this mAb with the FDA approved cytotoxic payload, mertansine (DM1), which blocks microtubulin polymerization and inhibits TNBC cell growth. The specific targeting, drug delivery and anti-tumor efficacy of the anti-CD47 ADC were investigated in vitro and in vivo. Furthermore, immune response analysis detected an increase of immune cells in lymph nodes but no general immune toxicity in the immunocompetent xenograft model. The developed anti-CD47 ADC could provide a novel promising targeted treatment, with further development, to potentially treat drug-resistant TNBCs.

Materials and Methods

Cell Lines and Media

Multiple human TNBC cell lines including MDA-MB-468, MDA-MB-231 (ATCC, Manassas, VA) and MDA-MB-231-FLuc (GenTarget, San Diego, CA), mouse TNBC cell line 4T1-Luc (ATCC), and normal breast epithelium cell lines 184B5 and MCF-10A were used in the in vitro or in vivo evaluation studies of the developed anti-CD47 mAb and ADC. The TNBC cells were maintained in DMEM/F12 medium supplemented with 4 g/L of glucose, 4 mM of L-glutamine, and 10% of fetal bovine serum (FBS, v/v) in T25, T75 or T175 flasks. The normal 184B5 and MCF-10A cells were maintained in MEGM bullet kit growth medium (Lonza, Walkersville, MD) supplemented with 5% of FBS. The hybridoma cells producing anti-CD47 mAb were cultivated in DMEM with 4 g/L of glucose, 4 mM of L-glutamine, and 10% of FBS in T flasks, or adapted in Hybridoma-SFM (serum free medium) in shaker flasks with agitation of 130 rpm. The seed cultures were incubated at 37° C. and 5% $CO_2$ in a humidified incubator (Caron, Marietta, Ohio). All media, supplements, and bioreagents used in this study were purchased from Fisher Scientific (Waltham, MA) unless otherwise specified.

Anti-CD47 mAb Development and Production

The mAb that targets the 1$^{st}$ extracellular domain (Gln19-Glu141) of membrane CD47 was developed using hybridoma technology as we published before (Si, Y.; et al. Cancer Gene Therapy. Cancer Gene Therapy 2020). Briefly, mFc fused peptide (Gln19-Glu141) was expressed in HEK293 cells through transient transfection, purified using protein G, and used to immunize mice. After detecting anti-CD47 mAb in serum, the splenocytes were harvested and fused with myeloma Sp2/0-Ag14 to generate hybridoma. The top clone was screened using ELISA and adapted to serum-free suspension culture to produce mAb. The anti-CD47 mAb was produced in 30-1,000 mL culture at Temp 37° C. and agitation 80-130 rpm. The bioproduction was seeded with viable cell density (VCD) of 0.3-0.5×10⁶ cells/mL in Hybridoma-SFM fed with glucose and L-glutamine to maintain the culture concentration within 2-4 g/L and 2-4 mM, respectively. The produced mAb was purified using liquid chromatography system (Bio-Rad, Hercules, CA) equipped with Protein A column (i.e. Bio-Scale Mini UNOsphere SUPrA affinity chromatography cartridges, Bio-Rad) (Ou, J.; et al. PLoS One 2018, 13:e0206246; Xu, N.; et al. Biochemical Engineering Journal 2019, 145:177-185), and characterized using SDS-PAGE. The isotype of the CD47 mAb was determined using a mouse antibody isotyping kit (Sigma, St. Louis, MO).

ADC Construction and Analysis

The anti-CD47 mAb-DM1 was constructed following a published conjugation procedure (Si, Y.; et al. Eng Life Sci 2021, 21:37-44; Ou, J.; et al. PLoS One 2018, 13:e0206246; Xu, N.; et al. Biochemical Engineering Journal 2019, 145: 177-185) with optimized conditions. Briefly, 10 mg/mL of CD47 mAb, 22.9 mM of Sulfo-SMCC linker and 10 mM of DM1 stocks were mixed with molar ratio of 1:14:18.2. The working concentration of antibody was 1 mg/mL. After 2-hr reaction at room temperature, the free linkers and unconjugated drug were removed with 10 kDa MWCO PES concentrator, and the unconjugated mAb and constructed ADC were further purified by liquid chromatography system with protein A column. The system was equilibrated with buffer A comprised of 0.02 M sodium phosphate and 0.02 M sodium citrate at pH 7.5, and the anti-CD47 mAb/ADC were eluted with buffer B containing 0.02 M sodium citrate and 0.1 M sodium chloride at pH 3.0. The purified ADC was neutralized to pH 7.0 with 1 M Tris solution, desalted and buffer exchanged using 10 kDa MWCO PES concentrator, sterilized, and mixed with 0.02% sodium azide for long-term storage at −80° C. The purity and drug-antibody ratio (DAR) analysis were performed using HPLC (Shimadzu, Columbia, MD) equipped with MAbPac HIC-Butyl column (5 µm, 4.6×100 mm). The mobile phase A comprised of 2 M ammonium sulfate and 100 mM sodium phosphate at pH 7.0 and B comprised of 100 mM sodium phosphate at pH 7.0 were applied at room temperature with flow rate of 1.0 mL/min. The same HPLC column and mobile phases can be used to isolate ADC from unconjugated mAb if the antibody-drug conjugation efficiency is <95%. The integrity of ADC was confirmed with SDS-PAGE.

SDS-PAGE and Western Blots

The non-reducing SDS-PAGE was run by loading 2 µg of mAb or ADC to Bolt™ 4 to 12%, Bis-Tris Mini Protein Gel (1.0 mm) to validate the purity and integrality of the produced anti-CD47 mAb and ADC. In Western blotting analysis, 30 µg of total cell lysis protein was loaded to gel and electro-transferred to PVDF membrane using PowerEase™ Touch 350 W Power Supply (Fisher). After blocking, the blotted membrane was probed using primary rabbit anti-mouse antibody and HRP-conjugated secondary anti-rabbit antibody (Abcam, Cambridge, UK). The blotted membrane was treated with Luminata Forte Western HRP substrate (Millipore, Boston, MA). The SDS-PAGE and Western blots were imaged with MyECL imager and quantified using ImageJ software.

Flow Cytometry

The flow cytometry was conducted to analyze anti-CD47 mAb's binding rate to TNBC cells and quantify the immune cells using a BD LSRII flow cytometer (BD Biosciences, San Jose, CA). In surface binding analysis, the produced CD47 mAb was labelled with an Alexa Fluor™ 647 labelling kit (Life Technologies, part of Fisher) and used to stain MDA-MB-468, MDA-MB-231, 4T1, and 184B5 cells with 5 µg of mAb-AF647 per million of cells at room temperature for 30 mins (Ou, J.; et al. PLOS ONE 2018; Si, Y.; et al. Pharmaceutics 2020, 12:1079-1090; Ou, J.; et al. J Biol Eng 2019, 13:34). The harvested lymph nodes were dissociated with Tissue Dissociation/Single Cell Isolation Kit (101 Bio LLC, Sunnyvale, CA) following manufacturing procedure, and stained with Cy5 anti-CD69 antibody, APC anti-CD11c antibody, or PE/Cy7 anti-CD4 antibody (BioLegend, San Diego, CA) for flow cytometry analysis.

Live-Cell Confocal Imaging

Confocal microscopy imaging was collected to validate the targeting and internalization of anti-CD47 mAb in TNBC cells following our reported protocol (Si, Y.; et al. Cancer Gene Therapy. Cancer Gene Therapy 2020; Si, Y.; et al. Eng Life Sci 2021, 21:37-44; Ou, J.; et al. PLOS ONE 2018; Si, Y.; et al. Pharmaceutics 2020, 12:1079-1090; Si, Y.; et al. Biotechnol J 2019). Briefly, the MDA-MB-468 cells were stained with BacMam GFP Transduction Control, which expresses eGFP protein in cytoplasm, NucBlue Live ReadyProbes to stain nucleus, and AF647 labelled anti-CD47 mAb to target TNBC cells via surface receptor. The live-cell images were collected using a Nikon A1R-HD25 confocal microscope with a high-speed resonance scanner (Nikon USA, Melville, NY).

CD47 Binding Affinity Analysis

The binding affinity of mAb-CD47 receptor was tested by measuring the dissociation constant ($K_D$) following reported procedure (Friguet, B.; et al. J Immunol Methods 1985, 77:305-319). Briefly, the 96-well plate was coated with 200 ng of CD47 receptor in 100 µL of coating buffer (50 mM carbonate-bicarbonate buffer, pH 9.6) and incubated at 4° C. overnight. The plate was washed three times with PBS containing 0.05% Tween 20, and blocked with 2% BSA (bovine serum albumin). Then 100 µL of three equilibrated reactions of anti-CD47 mAb and receptor with nanomolar ratios of 2.22:4.44, 3.33:3.33 and 4.44:2.22 and anti-CD47 mAb with concentrations of 0, 1, 5, 10, 20, 40, 80, 160, 320, 640 nM (for standard curve generation) were added into each well. After incubating at 37° C. for 1 hr, 100 µL of HRP goat anti-mouse IgG secondary antibody (Abcam, Cambridge, MA) at concentration of 50 ng/mL was added to each well and incubated at 37° C. for 1 hr, followed with TMB substrate for color development. The reaction was stopped by adding 100 µL of 1M sulfuric acid. The absorbance was recorded with BioTek plate reader at a wavelength of 450 nm.

In Vitro Cytotoxicity Assay

The 96-well plates were seeded with MDA-MB-231 and MDA-MB-468 cells at VCD of 5×10⁵ cells/mL in 100 µL of DMEM/F12 complete medium with triplication. Then 100 µL of cell growth medium containing ADC or free drug was added to reach final concentrations of 0-200 nM and incubated in $CO_2$ incubator for 72 hrs. The cytotoxicity of ADC or free drug was measured with CellTiter-Glo Luminescent Cell Viability Assay (Promega, Madison, MI) and reported as the relative viability using untreated cells as control. The $IC_{50}$ value was calculated using ED50V10 Excel add-in.

Whole Blood Analysis

The blood samples were extracted by cardiac puncture for whole blood analysis using HemaVet 950FS (Drew Scientific, Miami Lakes, FL). The leukocytes (white blood cell, neutrophil, lymphocyte, monocyte, eosnophils), erythrocytes (red blood cell, hemoglobin, mean corpuscular hemoglobin), and thrombocytes (platelet) were titrated to analyze the general peripheral immune response.

Primary TNBC Xenograft Model Generation

Human TNBC xenograft mouse model was generated by subcutaneously (s.c.) injecting $3\times10^6$ of MDA-MB-231-FLuc cells into the 6-week-old NSG (NOD scid gamma) female mice (Jackson Labs, Bar Harbor, ME). This immunocompromised model was used to evaluate the tumor targeting of our mAb and anti-TNBC efficacy of the constructed ADC. The immunocompetent mouse model was generated by injecting $1\times10^6$ of mouse TNBC 4T1-FLuc cells into the BALB/cJ female mice, which was used to analyze the tumoral immunity. Mice developed tumors within 2 weeks post cells injection.

In Vivo Imaging System (IVIS) Imaging

When TNBC tumor volume reached approximately 100 $mm^3$, 50 μg of Cyanine 5.5 (Cy5.5, Lumiprobe, Hunt Valley, MD) labelled anti-CD47 mAb or 1.5 nmole Cy5.5 (control, similar amount as labelled Cy5.5 in mAb) was intravenously (i.v.) administered via tail vein for TNBC-targeting analysis. Mice were imaged at 24 hrs post mAb injection under IVIS Lumina Series III (PerkinElmer, Waltham, MA) with wavelength of 660 nm/710 nm (excitation/emission) and exposure time of 10 seconds. Inhalation anesthesia was induced by delivering 3.5-4.5% isoflurane in oxygen to mice via respiratory system (nose cone), then maintained with a concentration of 1-2% during imaging procedure.

In Vivo Anti-TNBC Efficacy Study

The TNBC MDA-MB-231-FLuc xenograft mice were treated with 16 mg/kg-BW of GC by intraperitoneal (IP) injection when tumor volume reached ~50 $mm^3$. When tumor volume reached approximately 100 $mm^3$, mice were randomized into four groups (n=5) and treated with i.v. administration of PBS, 8 mg/kg of CD47 mAb, 8 mg/kg and 24 mg/kg of anti-CD47 ADC on a Q4D×4 schedule (4-day interval for 4 injections). Tumor volume was measured using an electronic caliper and calculated as "width×width×length/2" in mm. Body weight was measured every other day. The in vivo treatment study was ended after 21-day treatment which was determined based on our previous ADC treatment animal study (Si, Y.; et al. Eng Life Sci 2021, 21:37-44; Ou, J.; et al. PLoS One 2018, 13:e0206246; Xu, N.; et al. Biochemical Engineering Journal 2019, 145:177-185). At the end of the experiment, mice were euthanized and the TNBC tumors were collected to measure the wet weight.

Hematoxylin and Eosin (H&E) Staining

The IHC and H&E staining were performed. In IHC staining, the paraffin-embedded slides were immersed in xylene followed by 3% $H_2O_2$ in PBS, and blocked with 3% normal goat serum. The rabbit anti-mouse CD11b mAb (Cell Signaling, Danvers, MA) and HRP-conjugated goat anti-rabbit IgG mAb were used to stain the macrophage in tumor tissue. After color development with DAB chromogen, the slides were counterstained with hematoxylin and dehydrated in absolute ethanol. In H&E staining, the embedded normal organ slides were dewaxed, hydrated with 100%-0% ETOH, immersed in hematoxylin solution, and rinsed with tap water and eosin. After equilibration in ethanol, the stained slides were dipped in Xylene and mounted with cytoseal Xyl.

Statistical Analysis

The in vivo sample size was determined following our previous ADC therapy studies (Si, Y.; et al. Cancer Gene Therapy. Cancer Gene Therapy 2020; Si, Y.; et al. Eng Life Sci 2021, 21:37-44; Ou, J.; et al. PLOS ONE 2018). All numerical data were presented as mean±standard error of the mean (SEM). The significance of differences among groups was analyzed using a one-way ANOVA followed by post-hoc (Dunnett's) analysis. Statistical analysis was performed using GraphPad Prism and *$P<0.005$ was considered for all tests.

Results and Discussion

Both literature and our study revealed that the expression of surface receptor CD47 is upregulated post chemotherapy. This study developed and evaluated an anti-CD47 mAb-based ADC to treat TNBCs via surface targeting CD47 and delivering potent DM1 intracellularly. The immune response post ADC injection was also observed.

CD47 Expression in TNBC

The surface expression of CD47 in TNBC cell lines was analyzed using mass spectrometry (MS, Thermo Orbitrap Velos Pro) at the University of Alabama at Birmingham (UAB) MS and proteomics core facility. It was found that the normal breast cell MCF-10A had undetectable CD47 surface expression while TNBC cells, including MDA-MB-468, MDA-MB-157, MDA-MB-453, MDA-MB-231, BT-20 and BT-549, showed relative CD47 surface expression of 2-5 (FIG. 1B). Furthermore, to confirm the CD47 upregulation by chemotherapy, we treated MDA-MB-231 cells with 10 nM GC for 3 weeks. The Western blotting analysis showed that CD47 expression was increased in the GC-treated cells (FIG. 10). These data confirmed the literature finding that CD47 was upregulated by chemotherapies (Samanta, D.; et al. Proc Natl Acad Sci USA 2018, 115:E1239-E1248; Nigro, A.; et al. Front Immunol 2019, 10:3135) and could be a suitable target to develop a targeting strategy (ADC) for TNBC.

Development and Characterization of Anti-CD47 mAb and ADC

Figure 2A:
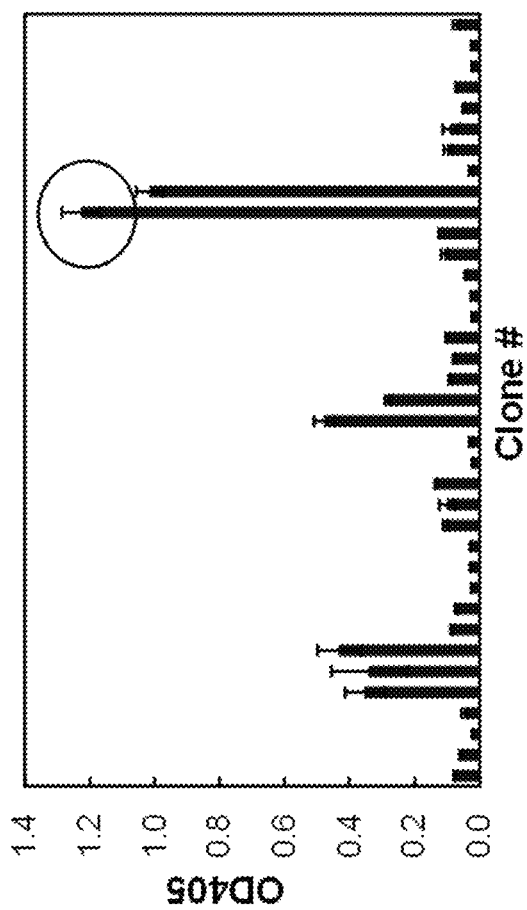
FIGS. 2A to 2D show anti-CD47 mAb and ADC development.
Figure 2B:
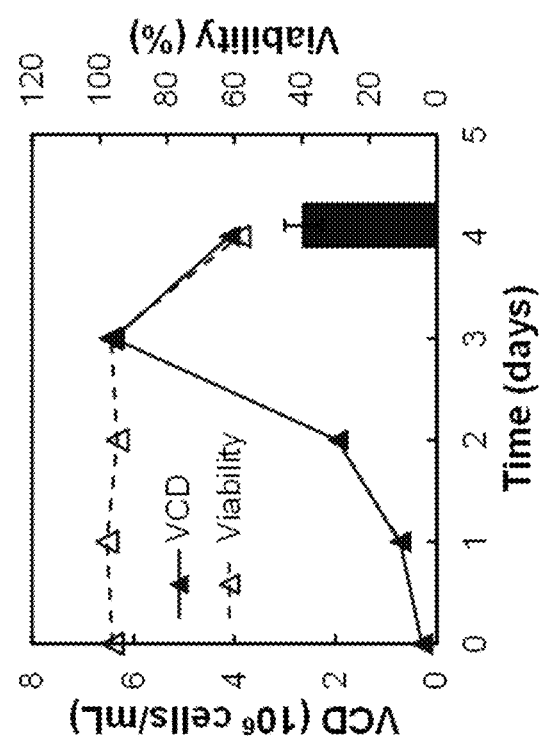

The top CD47 hybridoma clone was screened with ELISA analysis using HEK293 expressed peptide (Gln19-Glu141) as coating antigen (FIG. 2A). We further adapted CD47 mAb producing hybridama from adherent culture to suspension culture in serum free medium. The fed-batch bioproduction in Hybridoma-SFM reached maximal VCD of $6.4\times10^6$ cells/mL and average final titer of 32.5 mg/L (FIG. 2B). The isotype analysis revealed that the developed CD47 mAb was IgG2b/kappa. Additionally, affinity assay showed that the purified mAb had equilibrium dissociation constant ($K_D$) of 2.3 nM, suggesting a high surface receptor binding affinity of our anti-CD47 mAb.

Figure 2D:
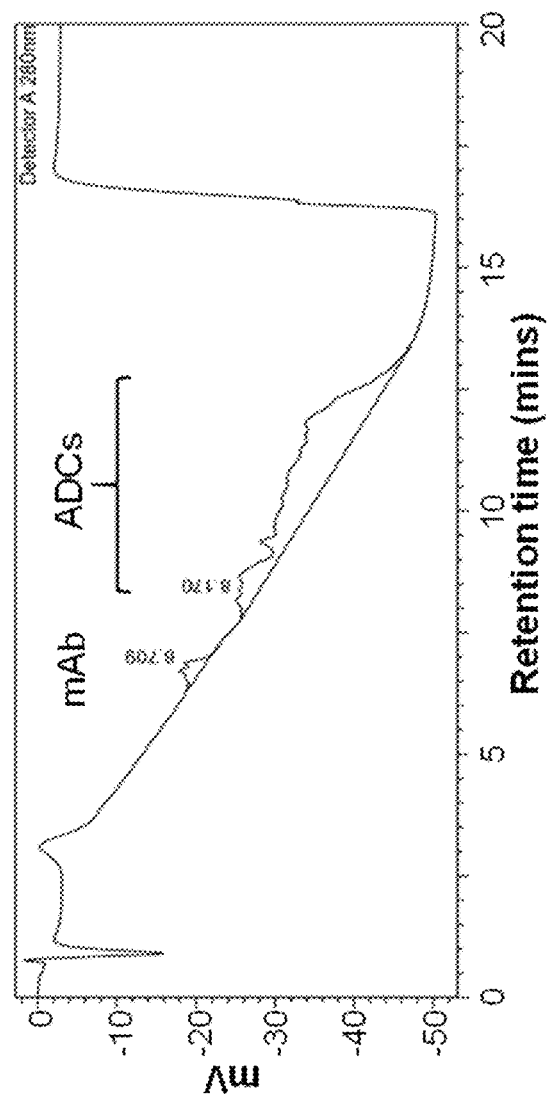
Figure 2C:
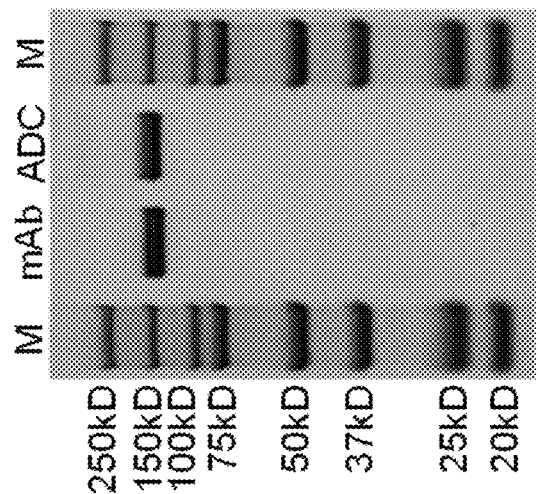

The purified CD47 mAb with protein A column was conjugated with DM1 to construct ADC for TNBC treatment. The SDS-PAGE analysis confirmed the mAb's molecular weight of 150 kDa and ADC of >150 kDa due to drug conjugation (FIG. 2C), which is consistent with our previously established ADC conjugation platform (Si, Y.; et al. Cancer Gene Therapy. Cancer Gene Therapy 2020). The conjugation rate and DAR analysis using HPLC with MAbPac HIC-Butyl column showed that mAb-drug conjugation rate was >95% and the average DAR of anti-CD47 ADC was 4-5 (FIG. 2D). These data demonstrated that the anti-CD47 mAb-DM1 conjugate was successfully constructed with high yield, conjugation efficiency and good integrity. The developed mAb and ADC were further evaluated in this study for TNBC targeting and treatment both in vitro and in vivo.

Surface Binding and Tumor Targeting

Figure 3A:
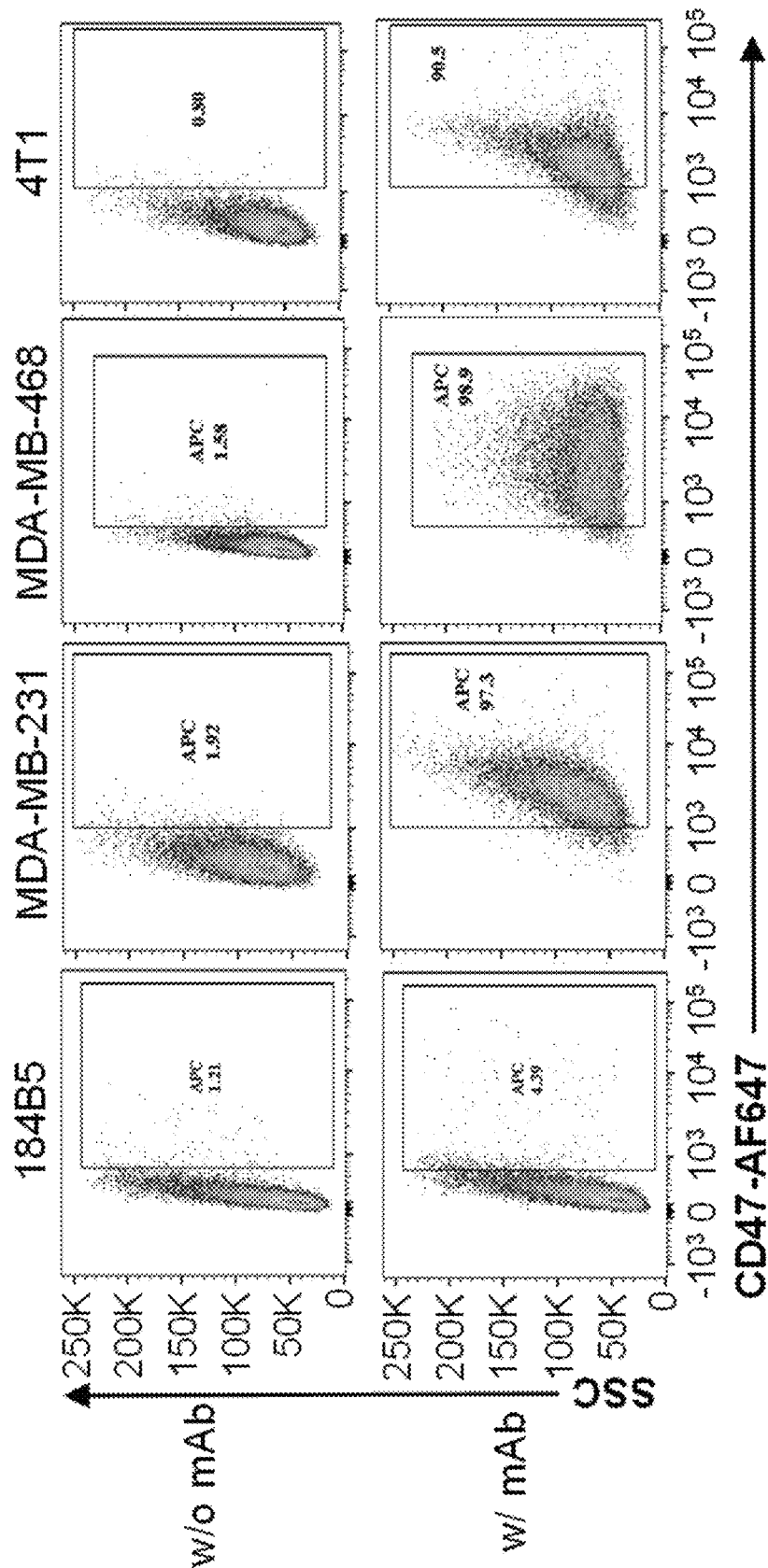
FIGS. 3A and 3B show in vitro surface binding and internalization of anti-CD47 mAb.

Flow cytometry analysis: To assess the in vitro TNBC targeting capability of the anti-CD47 mAb, flow cytometry analysis was first ran using normal breast 184B5 cells, human TNBC MDA-MB-231 and MDA-MB-468 cells, and mouse TNBC 4T1 cells (FIG. 3A). The CD47 mAb showed high surface binding to MDA-MB-231 and -468 cells (97.3% and 98.9%, respectively) and 4T1 cells (90.5%) but low binding to normal 184B5 cells (4.39%), indicating a high TNBC targeting capability. Human CD47 (UniProtKB Q61735) and mouse CD47 (UniProtKB Q08722) have the same topology including three extracellular, five helical transmembrane, and three cytoplasmic domains. Protein BLAST analysis showed that the 1$^{st}$ extracellular domain of human and mouse CD47 receptors have similarity of 76%. The flow cytometry data suggested that our anti-CD47 mAb targeted both human and mouse TNBC cells with high binding rate, so it is feasible to use human TNBC xenograft mouse model to evaluate the tumor targeting of the new mAb in vivo.

Figure 3B:

Confocal microscopy: Furthermore, the live-cell confocal microscopy imaging showed that the AF647 labelled anti-CD47 mAb effectively internalized into MDA-MB-468 cells via endocytosis and localized in the cytoplasm (detected with BacMam GFP) within 60 mins after mixing (FIG. 3B). These data indicated that the CD47 mAb can effectively target and internalize into TNBC cells.

IVIS imaging: The in vivo TNBC targeting of Cy5.5-labeled anti-CD47 mAb was evaluated using MDA-MB-231-FLuc xenograft model. Live-animal IVIS imaging revealed that our mAb (indicated by Cy5.5 fluorescence) targeted and accumulated in TNBC tumor (indicated by FLuc bioluminescence) within 24 hrs post i.v. injection (FIG. 4A). There was no obvious distribution of mAb in major organs such as brain, heart, lung, spleen, kidney and liver. The same amount of Cy5.5 dye was used as control and i.v. injected into MDA-MB-231-FLuc xenograft model. The fluorescent dye without targeted mAb distributed in multiple locations such as brain, liver and kidney. Altogether, these data suggested that the developed anti-CD47 mAb can effectively target TNBC cells or tumors, indicating its drug delivery capability.

In Vitro Anti-TNBC Cytotoxicity

The in vitro anti-cancer cytotoxicity of the constructed anti-CD47 mAb-DM1 (ADC) was tested using TNBC MDA-MB-231 and MDA-MB-468 cell lines and free drug DM1 as control. Multiple doses of ADC were tested including 0, 0.5, 1, 2, 5, and 10 nM. In the end of 3-day assay, MDA-MB-468 cell viability decreased to 100%, 67%, 54%, 48%, 34%, and 29% and MDA-MB-231 cell viability decreased to 100%, 95%, 80%, 71%, 67% and 67%, respectively (FIG. 5A). The free drug at doses of 0, 25, 50, 100, and 200 nM reduced MDA-MB-468 cell viability to 100%, 56%, 37%, 32%, and 34% and MDA-MB-231 cell viability to 100%, 94%, 72%, 53% and 54%, respectively (FIG. 5B). The IC$_{50}$ values of ADC were 0.3 nM and 0.8 nM and IC$_{50}$ values of DM1 were 21 nM and 47 nM for MDA-MB-468 and MDA-MB-231, respectively. These data indicated that the conjugation of DM1 to anti-CD47 mAb increased the cytotoxicity, likely due to the high TNBC-targeting and drug delivery efficiency of mAb. It is also found that the MDA-MB-468 cell line was more sensitive to ADC and DM1 than MDA-MB-231.

In Vivo Anti-Tumor Efficacy

To mimic chemotherapy in clinics, the xenograft mice were first treated with chemotherapy, i.e. 16 mg/kg of GC. When MDA-MB-231-FLuc xenografts reached ~100 mm$^3$, mice were treated with anti-CD47 ADC (8 and 24 mg/kg), anti-CD47 mAb (8 mg/kg, control), or PBS (vehicle, control) on a Q4D×4 schedule (i.e. Days 6, 10, 14 and 18) in four groups (n=5). FIG. 6A showed that TNBC tumor growth rate was significantly reduced by 52% in 8 mg/kg ADC group and 71% in 24 mg/kg ADC group as compared to PBS control group (p≤0.005). The tumor weight in 8 mg/kg mAb group was 307±76 g, which had no significant difference compared to that (362±162 g) in PBS group. The wet weight of terminal tumor in the 8 and 24 mg/kg ADC groups was 65% and 77% lower than PBS group (FIG. 6B), which confirmed the treatment efficacy of ADC. As expected, there was no obvious difference among the four groups in overall body weight change (FIG. 6C), suggesting that the toxicity of ADC was limited or well tolerated. To further evaluate the toxicity of TNBC treatment using anti-CD47 ADC, the important organs, such as brain, heart, lung, kidney, liver and spleen, were collected when the mice were sacrificed, sectioned and analyzed using hematoxylin and eosin (H&E) staining. As shown in FIG. 6B, none of these organs in the mice treated with 24 mg/kg of ADC had obvious morphology change or necrosis as compared to PBS control group, indicating no evident off-target effects in vivo. These in vivo anti-TNBC efficacy data support the hypothesis that the anti-CD47 ADC is an effective drug delivery vehicle with minimal toxicity. Moreover, the anti-CD47 ADC was effective for chemotherapy-treated TNBC, which could be further developed as a novel therapy for TNBC.

General Immune Response

The general immune response to anti-CD47 mAb was also tested using whole blood analysis and flow cytometry analysis of lymph nodes in the 4T1 xenograft BALB/cJ model (n=4). The mice carrying 50 mm$^3$ xenograft were treated with 8 mg/kg anti-CD47 mAb. After two weeks, blood was collected through cardiac puncture. The whole blood analysis using HemaVet 950FS showed that the leukocytes (white blood cell, neutrophil, lymphocyte, monocyte, eosnophils), erythrocytes (red blood cell, hemoglobin, mean corpuscular hemoglobin), and thrombocytes (platelet) counts had no obvious difference between the mAb group and PBS control group (FIG. 7A). These data indicated that the anti-CD47 mAb did not cause general peripheral immune toxicity. The lymph nodes were also harvested and dissociated for flow cytometry analysis of fresh cells. It was found that the CD69$^+$ NK, CD11c$^+$ DC and CD4$^+$ T cells were increased to 10.3%, 8.49% and 68.3% in mAb group from 6.55%, 5.44% and 63.8% in PBS control group (FIG. 7B). These data demonstrated that our anti-CD47 mAb can cause immune response but with low immune toxicity. In the future, a full investigation of immune function in tumor microenvironment is needed in order to delineate the possible anti-TNBC immunity of this mAb.

Conclusions

In this study, a new mAb and ADC was developed that targets the extracellular domain of the surface receptor CD47 to treat TNBC post standard chemotherapy. The constructed anti-CD47 ADC effectively targeted TNBC cells and tumor, released potent drugs intracellularly, and significantly inhibited the tumor growth post GC treatment in a xenograft model with minimal side effects.

Drug resistance and distant metastasis pose major challenges in the standard chemotherapy of TNBC. The developed anti-CD47 ADC has great potential to be further developed as a new targeted therapy for TNBC, especially post primary and chemotherapeutic treatments at time of recurrence. Furthermore, the anti-CD47 ADC could integrate multiple possible anti-cancer mechanisms: 1) direct TNBC cell death caused by potent drug DM1 which has been used to treat other cancers via blocking microtubulin polymerization, 2) increase phagocytosis of CD47-positive TNBC cells (which needs further evaluation), and 3) potentially overcome the challenge of drug resistance in chemotherapy. These advantages can be combined with other therapies to clear TNBC cells in vivo.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

SEQUENCE LISTING

```
Sequence total quantity: 10
SEQ ID NO: 1              moltype = AA  length = 474
FEATURE                   Location/Qualifiers
source                    1..474
                          mol_type = protein
                          organism = synthetic construct
SEQUENCE: 1
MLLGLKWVFF VVFYQGVHCE VQLVESGGGL VQPKGSLKLS CAASGFTFNT YAMNWVRQAP   60
GKGLEWIARI RSKSNNYATY YADSMKDRFT ISRDDSQSML YLQMNNLKTE DTAMYYCVRP  120
AQGAMDYWGH GTSVTVSSSK TTPPSVYPLA PGCGDTTGSS VTLGCLVKGY FPESVTVTWN  180
SGSLSSSVHT FPALLQSGLY TMSSSVTVPS STWPSQTVTC SVAHPASSTT VDKKLEPSGP  240
ISTINPCPPC KECHKCPAPN LEGGPSVFIF PPNIKDVLMI SLTPKVTCVV VDVSEDDPDV  300
QISWFVNNVE VHTAQTQTHR EDYNSTIRVV STLPIQHQDW MSGKEFKCKV NNKDLPSPIE  360
RTISKIKGLV RAPQVYILPP PAEQLSRKDV SLTCLVVGFN PGDISVEWTS NGHTEENYKD  420
TAPVLDSDGS YFIYSKLNMK TSKWEKTDSF SCNVRHEGLK NYYLKKSFSR TPGK        474

SEQ ID NO: 2              moltype = AA  length = 234
FEATURE                   Location/Qualifiers
source                    1..234
                          mol_type = protein
                          organism = synthetic construct
SEQUENCE: 2
MVFTPQILGL MLFWISASRG DIVLTQSPAT LSVTPGDSVS LSCRASQRIS NNLHWYQQKS   60
HESPRLLIKY SSQSISGIPS RFSGSGSGTD FTLSINSVET EDFGMYFCQQ SNAWPYTFGG  120
GTKLEIRRAD AAPTVSIFPP SSEQLTSGGA SVVCFLNNFY PKDINVKWKI DGSERQNGVL  180
NSWTDQDSKD STYSMSSTLT LTKDEYERHN SYTCEATHKT STSPIVKSFN RNEC        234

SEQ ID NO: 3              moltype = AA  length = 119
FEATURE                   Location/Qualifiers
source                    1..119
                          mol_type = protein
                          organism = synthetic construct
SEQUENCE: 3
EVQLVESGGG LVQPKGSLKL SCAASGFTFN TYAMNWVRQA PGKGLEWIAR IRSKSNNYAT   60
YYADSMKDRF TISRDDSQSM LYLQMNNLKT EDTAMYYCVR PAQGAMDYWG HGTSVTVSS   119

SEQ ID NO: 4              moltype = AA  length = 108
FEATURE                   Location/Qualifiers
source                    1..108
                          mol_type = protein
                          organism = synthetic construct
SEQUENCE: 4
DIVLTQSPAT LSVTPGDSVS LSCRASQRIS NNLHWYQQKS HESPRLLIKY SSQSISGIPS   60
RFSGSGSGTD FTLSINSVET EDFGMYFCQQ SNAWPYTFGG GTKLEIRR              108

SEQ ID NO: 5              moltype = AA  length = 9
FEATURE                   Location/Qualifiers
source                    1..9
                          mol_type = protein
                          organism = synthetic construct
SEQUENCE: 5
FTFNTYAMN                                                           9

SEQ ID NO: 6              moltype = AA  length = 16
FEATURE                   Location/Qualifiers
source                    1..16
                          mol_type = protein
                          organism = synthetic construct
SEQUENCE: 6
WIARIRSKSN NYATYY                                                  16

SEQ ID NO: 7              moltype = AA  length = 9
FEATURE                   Location/Qualifiers
source                    1..9
                          mol_type = protein
                          organism = synthetic construct
SEQUENCE: 7
RPAQGAMDY                                                           9

SEQ ID NO: 8              moltype = AA  length = 8
FEATURE                   Location/Qualifiers
source                    1..8
                          mol_type = protein
                          organism = synthetic construct
SEQUENCE: 8
QRISNNLH                                                            8
```

```
SEQ ID NO: 9             moltype = AA  length = 11
FEATURE                  Location/Qualifiers
source                   1..11
                         mol_type = protein
                         organism = synthetic construct
SEQUENCE: 9
LLIKYSSQSI S                                                                     11

SEQ ID NO: 10            moltype = AA  length = 8
FEATURE                  Location/Qualifiers
source                   1..8
                         mol_type = protein
                         organism = synthetic construct
SEQUENCE: 10
QQSNAWPY                                                                          8
```

What is claimed is:

1. An antibody that selectively binds CD47 on tumor cells, comprising a variable heavy ($V_H$) domain having complementarity determining region 1 (CDR1), CDR2 and CDR3 sequences and a variable light ($V_L$) domain having CDR1, CDR2 and CDR3 sequences, wherein the CDR1 sequence of the $V_H$ domain comprises the amino acid sequence FTFNTYAMN (SEQ ID NO:5), the CDR2 sequence of the $V_H$ domain comprises the amino acid sequence WIARIRSKSNNYATYY (SEQ ID NO:6), the CDR3 sequence of the $V_H$ domain comprises the amino acid sequence RPAQGAMDY (SEQ ID NO:7), the CDR1 sequence of the $V_L$ comprises the amino acid sequence QRISNNLH (SEQ ID NO:8), the CDR2 sequence of the $V_L$ domain comprises the amino acid sequence LLIKYSSQSIS (SEQ ID NO:9), and the CDR3 sequence of the $V_L$ domain comprises the amino acid sequence QQSNAWPY (SEQ ID NO:10).

2. The antibody of claim 1, wherein the $V_H$ domain comprises the amino acid sequence SEQ ID NO:3.

3. The antibody of claim 1, wherein the $V_H$ domain has at least 90% sequence identity to the amino acid sequence SEQ ID NO:3.

4. The antibody of claim 1, wherein the $V_L$ domain comprises the amino acid sequence SEQ ID NO:4.

5. The antibody of claim 1, wherein the $V_L$ domain has at least 90% sequence identity to the amino acid sequence SEQ ID NO:4.

6. The antibody of claim 1, wherein the antibody is a monoclonal antibody.

7. The antibody of claim 1, wherein the antibody is humanized.

8. The antibody of claim 1, wherein the antibody is a chimeric antibody.

9. The antibody of claim 1, wherein the antibody is conjugated to a cytotoxin to form an antibody-drug conjugate.

10. The antibody of claim 9, wherein the cytotoxin is selected from the group consisting of an auristatin, a calicheamicin, a maytansinoid, or a tubulysin.

11. The antibody of claim 9, wherein the cytotoxin is monomethylauristatin E, monomethylauristatin F, calicheamicin γ, mertansine, tubulysin T3, or tubulysin T4.

12. A method for therapeutically treating CD47-mediated cancer in a mammalian subject, comprising administering an effective amount of the antibody of claim 1 to the mammalian subject.

* * * * *